United States Patent [19]

Levitt

[11] Patent Number: 4,565,567

[45] Date of Patent: Jan. 21, 1986

[54] HERBICIDAL HETEROCYCLIC ALKYLAMINOCARBONYLSULFONAMIDES

[75] Inventor: George Levitt, Wilmington, Del.

[73] Assignee: E. I. Du Pont de Nemours and Company, Wilmington, Del.

[21] Appl. No.: 678,881

[22] Filed: Dec. 6, 1984

Related U.S. Application Data

[60] Division of Ser. No. 472,879, Mar. 14, 1983, Pat. No. 4,496,392, which is a continuation-in-part of Ser. No. 377,371, May 12, 1982, abandoned.

[51] Int. Cl.$^4$ .................. C07D 239/42; C07D 239/47; A01N 47/28

[52] U.S. Cl. ......................... 71/92; 544/320; 544/321; 544/331; 544/332

[58] Field of Search ................... 71/92; 544/320, 321, 544/331, 332

[56] References Cited

U.S. PATENT DOCUMENTS 4,514,211 4/1985 Rorer ................................... 71/92

Primary Examiner—Robert Gerstl

[57] ABSTRACT

Heterocyclic alkylaminocarbonylsulfonamides, such as N'-[(4,6-dimethylpyrimidin-2-yl)methylaminocarbonyl]-N,N-dimethyl-1,2-benzenedisulfonamide, are useful as herbicides.

19 Claims, No Drawings

HERBICIDAL HETEROCYCLIC ALKYLAMINOCARBONYLSULFONAMIDES

RELATED APPLICATION

This application is a divisional application of U.S. Ser. No. 472,879, filed Mar. 14, 1983 now U.S. Pat. No. 4,496,392, which is a continuation-in-part of my application U.S. Ser. No. 377,371, filed May 12, 1982, now abandoned.

BACKGROUND OF THE INVENTION

The present invention relates to a novel class of heterocyclic alkylaminocarbonylsulfonamides of the following formula:

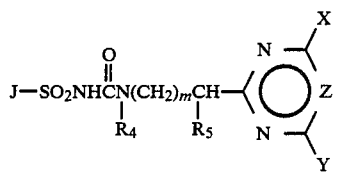

and further to the use of these compounds in agriculturally suitable compositions as pre-emergent or post-emergent herbicides or as plant growth regulants.

The following U.S. Patents disclose and claim various classes of herbicidal sulfonamides:

U.S. Pat. No. 4,169,719
U.S. Pat. No. 4,127,405
U.S. Pat. No. 4,190,432
U.S. Pat. No. 4,225,337
U.S. Pat. No. 4,257,802
U.S. Pat. No. 4,214,890
U.S. Pat. No. 4,310,346
U.S. Pat. No. 4,231,784

These herbicidal sulfonamides can be represented by the following general formula:

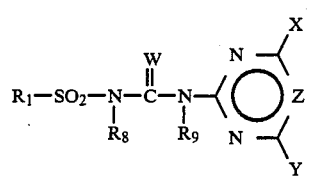

wherein
$R_1$ can be, among other substituents,

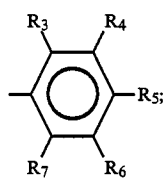

$R_3$, $R_4$, $R_5$, $R_6$ and $R_7$ can be H, halo or other values;
$R_8$ and $R_9$ can be H or $CH_3$;
W can be O; and
Z can be N or CH.

U.S. Pat. No. 4,420,325, issued Dec. 13, 1983 to Sauers discloses herbicidal benzylsulfonylureas of the general formula

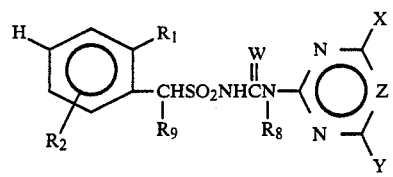

wherein
$R_1$ can be F, Cl, Br, $CF_3$, $C_1$-$C_3$ alkyl and $CO_2R_4$, among other values;
$R_2$ can be H, Cl, Br, F, $CF_3$ or $OCH_3$;
$R_4$ can be alkyl;
$R_8$ can be H or $CH_3$;
$R_9$ can be H or $C_1$-$C_3$ alkyl;
W is O or S; and
Z can be CH or N.

Although there are certain structural similarities between the art compounds and the compounds within the scope of the present invention, such as, for example, an ortho-substituted phenyl radical and symmetrical pyrimidine and triazine heterocycles, the compounds differ in the bridge structure. The art compounds have the following bridge structure

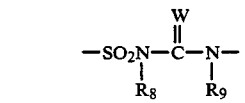

which may vary according to available substitutions on either nitrogen atom. The compounds within the scope of the present invention have the following bridge structure

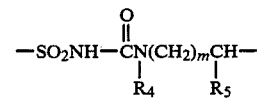

wherein
$R_4$ and $R_5$ can be H or $CH_3$; and
m can be 0 or 1.

SUMMARY OF THE INVENTION

This invention pertains to novel compounds of Formula I, to agriculturally suitable compositions containing them, and to their use as preemergent or postemergent herbicides or plant growth regulants.

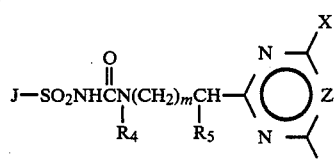

wherein
J is

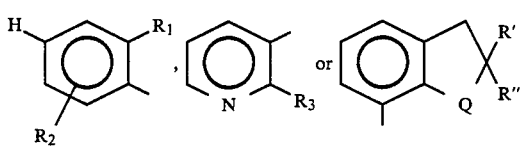

$R_1$ is $NO_2$, F, Cl, Br, $CF_3$, $C_1$–$C_3$ alkyl, $CH_2CH_2OCH_3$, $CO_2R_6$, $S(O)_nR_7$, $SO_2NR_8R_9$, $SCF_2H$, $OR_{10}$, $OSO_2R_{11}$, $SO_2N(CH_3)$—$OCH_3$, $CH_2OCH_3$, $CH_2OCH_2CH_3$,

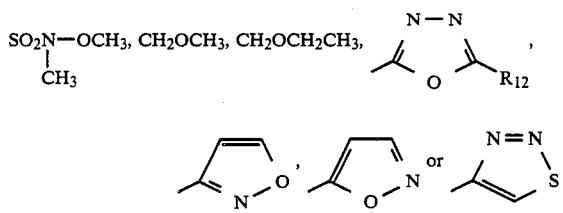

$R_2$ is H, F, Cl, Br, $CH_3$, $OCH_3$ or $CF_3$;
$R_3$ is Cl, $SO_2CH_3$ or $SO_2N(CH_3)_2$;
$R_4$ and $R_5$ are independently H or $CH_3$;
$R_6$ is $C_1$–$C_3$ alkyl, $CH_2CH=CH_2$, $CH_2CH_2Cl$ or $CH_2CH_2OCH_3$;
$R_7$ is $C_1$–$C_3$ alkyl or $CH_2CH=CH_2$;
$R_8$ is $CH_3$;
$R_9$ is $C_1$–$C_3$ alkyl;
$R_{10}$ is $C_1$–$C_3$ alkyl, $CF_2H$ or $CH_2CH_2OCH_3$;
$R_{11}$ is $C_1$–$C_3$ alkyl;
$R_{12}$ is H or $CH_3$;
n is 0 or 2;
m is 0 or 1;
Q is O, S or $SO_2$;
R' is H or $CH_3$;
R" is H or $C_1$–$C_3$ alkyl;
Z is CH or N;
X is $CH_3$ or $OCH_3$;
Y is $CH_3$, $C_2H_5$, $OCH_3$, $OC_2H_5$, $CH_2OCH_3$, $CH(OCH_3)_2$ or

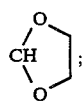

provided that
(1) $R_4$ and $R_5$ cannot simultaneously be $CH_3$ and when either $R_4$ or $R_5$ is $CH_3$, then $R_2$ must be H;
(2) when m is 1, then Z is N;
(3) when Z is CH, then $R_2$ is H;
(4) when X and Y are both $CH_3$ and Z is CH, then $R_1$ must be other than $NO_2$, $S(O)_nR_7$ or $C_1$–$C_3$ alkyl;
and their agriculturally suitable salts.

Preferred for their higher herbicidal activity, greater plant growth regulant activity and/or more favorable ease of synthesis are:
(1) Compounds of Formula I where $R_2$, $R_4$ and $R_5$ are H, m is O and X is $OCH_3$.
(2) Compounds of Preferred 1 where Y is $CH_3$, $C_2H_5$, $CH_3O$ or $C_2H_5O$.
(3) Compounds of Preferred 2 where J is

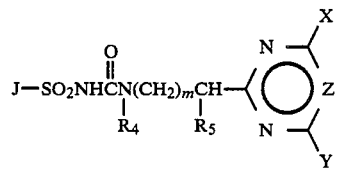

(4) Compounds of Preferred 3 where $R_1$ is $CO_2CH_3$, $CO_2C_2H_5$, $SCF_2H$, $OSO_2CH_3$ or $SO_2N(CH_3)_2$.
(5) Compounds of Preferred 4 where Y is $OCH_3$ and Z is N.

Specifically Preferred for their highest herbicidal activity, greatest plant growth regulant activity and/or most favorable ease of synthesis are:
Methyl 2-[N-[(4,6-dimethoxypyrimidin-2-yl)methylaminocarbonyl]aminosulfonyl]benzoate;
N'-[(4,6-Dimethylpyrimidin-2-yl)methylaminocarbonyl]-N,N-dimethyl-1,2-benzenedisulfonamide;
N'-[(4,6-Dimethoxypyrimidin-2-yl)methylaminocarbonyl]-N,N-dimethyl-1,2-benzenedisulfonamide;
N'-[(4,6-Dimethoxy-1,3,5-triazin-2-yl)methylaminocarbonyl]-N,N-dimethyl-1,2-benzenedisulfonamide; and
N'-[(4-Methoxy-6-methypyrimidin-2-yl)methylaminocarbonyl]-N,N-dimethyl-1,2-benzenedisulfonamide.

DETAILED DESCRIPTION OF THE INVENTION Synthesis

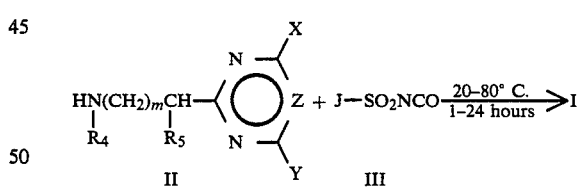

The compounds of Formula I may be prepared as shown below in Equation 1 by the reaction of an appropriate heterocyclic amine of Formula II with an appropriately substituted sulfonyl isocyanate, III.

EQUATION 1

$$HN(CH_2)_m\underset{R_4}{C}H-\underset{R_5}{\overset{}{}}\text{ring}-Z + J-SO_2NCO \xrightarrow[\text{1–24 hours}]{20-80^\circ \text{ C.}} I$$

II      III wherein
J, m, $R_4$, $R_5$, X, Y and Z are as previously defined.

The reaction of Equation 1 is best carried out in an inert aprotic solvent such as methylene chloride, tetrahydrofuran, or acetonitrile at temperatures between 20° and 80° C. A catalytic amount of 1,4-diazabicyclo[2.2.2]octane (DABCO) may be used to accelerate the reaction. In some cases, the products are insoluble in the reaction medium and may be isolated by simple filtration. Products soluble in the reaction medium are isolated by evaporation of the solvent, trituration of the residue with solvents such as 1-chlorobutane or diethyl ether, and filtration.

The heterocyclic amines of Formula IIa in which $R_4=R_5=H$ may be prepared as shown below in Equation 2 by catalytic hydrogenation of the appropriate heterocyclic nitriles of Formula IV in the presence of a mineral acid.

EQUATION 2

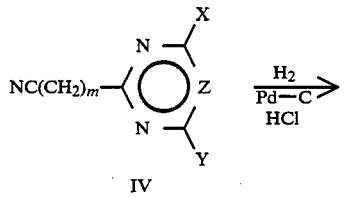

IV

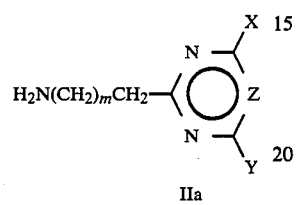

IIa wherein
m, X, Y and Z are as previously defined.

The reaction is best carried out by subjecting the nitriles of Formula IV to a hydrogen atmosphere of 40–50 p.s.i. at ambient temperature in the presence of 10% palladium-on-carbon catalyst and at least one equivalent of concentrated hydrochloric acid in an alcoholic solvent, e.g., methanol or ethanol. When hydrogen uptake has ceased, the reaction mixture is filtered. Adjustment of the filtrate to pH 10–12 with aqueous sodium hydroxide followed by extraction with methylene chloride or ether and evaporation of the solvent in vacuo gives the desired heterocyclic amines. In some cases, the product is insoluble in the basic aqueous layer and may be isolated by filtration.

The compounds of Formula IIb, where $R_4$=$CH_3$ and $R_5$=H, can be synthesized as shown in Equation 3 by treatment of the corresponding amines IIa ($R_4$=H) with formaldehyde followed by reduction with sodium cyanoborohydride.

EQUATION 3

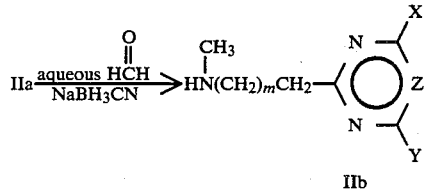

IIb wherein
m, X, Y and Z are as previously defined.

The reaction of Equation 3 is best carried out according to the procedure described by Borch and Hassid, J. Org. Chem., 37, 1673 (1972).

The compounds of Formula IIc in which $R_5$=$CH_3$, m=0 and $R_4$=H can be most conveniently prepared by the two-step sequence shown in Equation 4 below starting from the appropriate nitrile of Formula IVa (m=0).

EQUATION 4

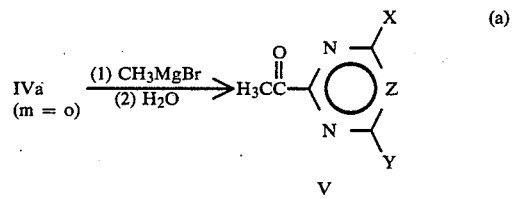

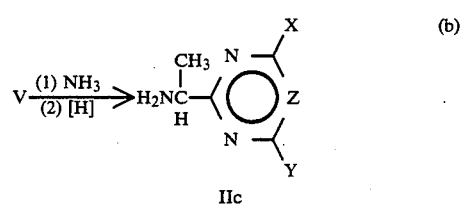

IIc wherein
X, Y and Z are as previously defined.

The addition of Grignard Reagents such as methylmagnesium bromide to nitriles with subsequent hydrolysis (as shown in Equation 4a) is well known in the literature as a method for synthesizing ketones. For relevant references, see Kharasch and Reinmuth, "Grignard Reactions of Nonmetallic Substances", New York: Prentice-Hall, Inc., 1954, pp. 767–845.

The reductive amination step shown in Equation 4b is best carried out by methods outlined in Wagner and Zook, "Synthetic Organic Chemistry", New York: John Wiley and Sons, Inc., 1953, pp. 662–663. Amines of Formula IIc may also be prepared from the corresponding ketones of Formula V according to the procedure of Borch (Org. Syn., 52, 124, (1972)).

Heterocyclic amines of Formula IId where m=1, $R_4$=H and $R_5$=$CH_3$ may be prepared as shown below in Equation 5 by hydrogenation of the unsaturated nitro compounds of Formula VI.

EQUATION 5

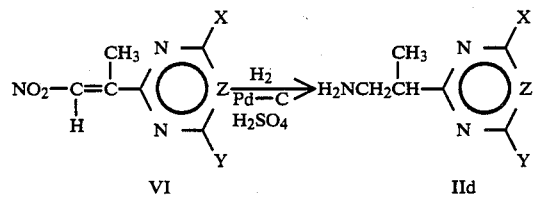

VI                              IId wherein
X, Y and Z are as previously defined.

Reductions of unsaturated nitro compounds are well known in the chemical literature. For pertinent examples, see H. O. House, "Modern Synthetic Reactions", 2nd Ed., Menlo Park, Calif.: W. A. Benjamin, Inc., 1972, pp. 1–18 and W. Carruthers, "Some Modern Methods of Organic Synthesis", 2nd Ed., New York: Cambridge University Press, 1978, p. 419.

Heterocyclic nitriles of Formula IVa where m=0 may be prepared as shown in Equation 6 by the reaction of an appropriate trimethylammonium salt of Formula VII with potassium cyanide according to the method of Klotzer (Monatsh., 87, 526;536 (1956)).

EQUATION 6

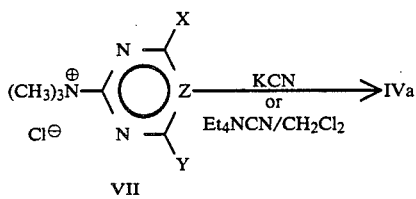

wherein

X, Y and Z are as previously defined.

The reaction of Equation 6 is preferably carried out by adding the trimethylammonium salts VII to a mixture of potassium cyanide in a suitable medium such as molten acetamide (at 85°–90° C.), dimethylformamide, or dimethyl sulfoxide. The solution is then stirred at elevated temperatures (50°–90° C.) for one hour. Water is added to the cooled mixture and the desired product is isolated by extraction into ether or methylene chloride followed by drying and evaporation of the solvent in vacuo. Alternatively, the trimethylammonium salts VII can be treated with one equivalent of tetraethylammonium cyanide in a suitable solvent such as methylene chloride at room temperature. For a closely related use of tetraethylammonium cyanide, see K. Hermann and G. Simchen, *Liebigs Ann. Chem.*, 333 (1981).

Compounds of Formula VII may be synthesized by the reaction of a chloro heterocycle of Formula VIII with trimethylamine as shown below in Equation 7.

EQUATION 7

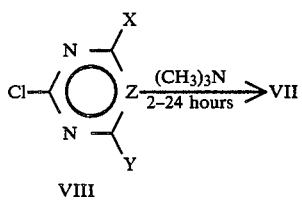

wherein

X, Y and Z are as previously defined.

The reaction of Equation 7 is typically effected by adding liquid anhydrous trimethylamine to a solution of the chloro heterocycle of Formula VIII at 0° C. in a suitable organic solvent such as acetone or tetrahydrofuran. The products are generally insoluble in the reaction medium and may be isolated by simple filtration.

Heterocyclic nitriles of Formula IVb where m=1 may be synthesized from the appropriate chloromethyl heterocycles of Formula IX as shown in Equation 8.

EQUATION 8

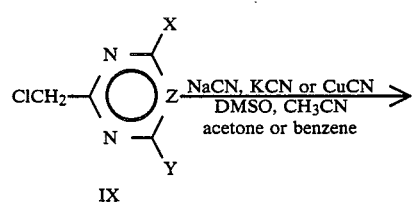

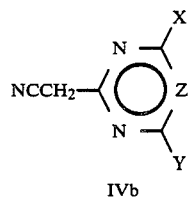

wherein

X, Y and Z are as previously defined.

Many examples of such a nucleophilic displacement with cyanide exist in the chemical literature, but the reaction can most conveniently be effected according to the procedures of L. Friedman and H. Schecter in *J. Org. Chem.*, 25, 877 (1960) or R. A. Smiley and C. Arnold, *J. Org. Chem.*, 25, 257 (1960).

The chloromethyl compounds of Formula IX can be prepared by the two-step procedure shown below in Equation 9 starting from appropriate 2-methyl heterocycles via halogenation of the corresponding N-oxides XI.

EQUATION 9

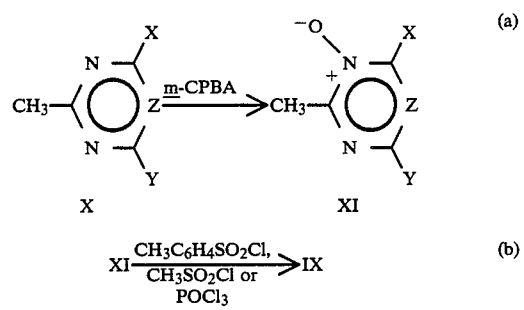

wherein

X, Y and Z are as previously defined.

N-Oxides of tertiary amines are readily formed upon treatment of the latter with m-chloroperoxybenzoic acid (m-CPBA) as shown in Equation 9a above. For relevant procedures, see J. C. Craig and K. K. Purushothaman, *J. Org. Chem.*, 35, 1721 (1970).

The reaction of Equation 9b, in which a chlorine atom is introduced onto the 2-methyl substituent with concomitant loss of the N-oxide oxygen atom, can be carried out according to the procedure described in the following references: L. Bauer and L. A. Gardella, *J. Org. Chem.*, 28, 1323 (1963); R. R. Hunt, J. F. W. McOmie and E. R. Sayer, *J. Chem. Soc.*, 525 (1959); and E. Matsumura, *Nippon Kagaku Zasshi*, 74, 363 (1953).

Unsaturated nitro heterocycles of Formula VI may be prepared in two-steps by addition of the nitromethane anion to ketones of general structure V and subsequent dehydration as shown below in Equation 10.

EQUATION 10

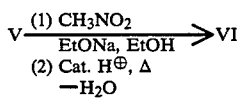

wherein

X, Y and Z are as previously defined.

The addition of nitromethane anion to ketones is well precedented in the literature and can be carried out according to the procedure described by H. J. Dauben, et al., in *Organic Synthesis, Coll. Vol.* 4, 221 (1963). Subsequent loss of water from the adduct of nitromethane anion and ketone V can be effected by heating at reflux temperature in a suitable solvent such as benzene or xylenes in the presence of a catalytic amount of an acid such as p-toluenesulfonic or camphorsulfonic acid. Water removal can be accomplished by use of a Dean-Stark water separator.

Methods for the preparation of 2-chloro heterocycles of Formula VIII are well precedented in the literature. For example, the synthesis of 2-chloro-4,6-dimethyl-pyrimidine (VIII; $X=Y=CH_3$, $Z=CH$) is described by St. Angerstein in *Ber. dtsch. Chem. Ges.*, 34, 3956 (1901).

For the preparation of both 2-chloro-4,6-dimethoxypyrimidine (VIII; $X=Y=OCH_3$, $Z=CH$) and 2-chloro-4-methyl-6-methoxypyrimidine (VIII; $X=CH_3$, $Y=OCH_3$, $Z=CH$), see Bee and Rose, *J. Chem. Soc.*, (c), 2031 (1966).

The preparation of 2-chloro-4,6-dimethoxytriazine (VIII; $X=OCH_3$, $Y=OCH_3$, $Z=N$) is described by Dudley, et al., *J. Am. Chem. Soc.*, 73, 2986 (1951).

The synthesis of 2-chloro-4-methyl-6-methoxytriazine (VIII; $X=CH_3$, $Y=OCH_3$, $Z=N$) is best carried out according to the procedure of Kobe, Stanornik, and Tisler, *Monatsh.*, 101, 724 (1970).

Methods for preparation of the requisite 2-methyl heterocycles (X) are also well precedented in the literature. For the synthesis of 2,4,6-trimethyl triazine (X; $Z=N$, $X=Y=CH_3$), see T. Carins, A. Larcher and B. McKusick, *J. Am. Chem. Soc.*, 74, 5633 (1952) and U.S. Pat. No. 2,503,999.

The preparation of 2-methyl-4,6-dimethoxy triazine (X; $Z=N$, $X=Y=OCH_3$) is described by N. V. Khromov-Borisov and E. V. Kisareva in *Zhur. Obshchei Khim.*, 29, 3010 (1959).

For the synthesis of 2,4-dimethyl-6-methoxy triazine (X; $Z=N$, $X=CH_3$, $Y=OCH_3$), see F. C. Schaefer, *J. Org. Chem.*, 27, 3608 (1962).

All of the above are herein incorporated by reference.

The synthesis of sulfonyl isocyanates such as those depicted by Formula III is best carried out according to the methods taught by the following:

U.S. Pat. No. 4,127,405 for isocyanates of Formula III where $J=R_2C_6H_3R_1$ and $R_1=NO_2$, F, Cl, Br, $C_1$-$C_3$ alkyl and $OR_{10}$;

European Pat. No. 23,141 for isocyanates of Formula III where $J=R_2C_6H_3R_1$ and $R_1=SO_2NR_8R_9$;

European Pat. No. 35,893 for isocyanates of Formula III where $J=R_2C_6H_3R_1$ and $R_1=S(O)_nR_7$;

European Pat. No. 7,687 for isocyanates of Formula III where $J=R_2C_6H_3R_1$ and $R_1=CO_2R_6$;

Sulfonyl isocyanates of Formula III where $J=R_2C_6H_3R_1$ and $R_1=CH_2CH_2OCH_3$ are synthesized by methods disclosed in copending patent application U.S. Ser. No. 416,563.

Sulfonyl isocyanates of Formula III where $J=R_2C_6H_3R_1$ and $R_1=$ 1,3,4-oxadiazol-5-yl, isoxazol-3, or 5-yl, or 1,2,3-thiadiazol-4-yl can be prepared by methods taught in copending patent application U.S. Ser. No. 436,631.

Sulfonyl isocyanates of Formula III where $J=$pyridin-3-yl and $R_3=Cl$ or $SO_2N(CH_3)_2$ may be synthesized according to procedures described in European Pat. No. 13,480;

European Pat. No. 35,893 teaches methods for preparation of isocyanates of Formula III where $J=$pyridin-3-yl and $R_3=SO_2CH_3$.

Sulfonyl isocyanates of Formula III where $J=$benzofuran (Q=O), benzothiophene (Q=S), or benzothiophene dioxide (Q=SO$_2$), may be synthesized according to methods disclosed in copending patent application U.S. Ser. No. 410,993.

Isocyantes of Formula III in which $J=R_2C_6H_3R_1$ and $R_1=OSO_2R_{11}$ may be prepared from the appropriate sulfonamides of Formula XII as shown in Equation 10.

EQUATION 10

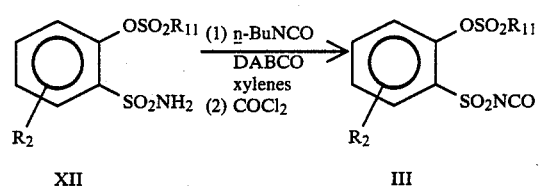

wherein $R_2$ and $R_{11}$ are as previously defined.

The reaction shown above is preferably carried out according to methods taught in U.S. Pat. No. 4,127,405. Sulfonamides of Formula XII can be conveniently synthesized as described in Research Disclosure, p. 52 (1978).

Sulfonyl isocyanates of Formula III in which $J=R_2C_6H_3R_1$ and $R_1=SCF_2H$ may be prepared from the corresponding nitro compounds XIII as shown in Equation 11 below according to procedures described in European Pat. No. 23,422.

EQUATION 11

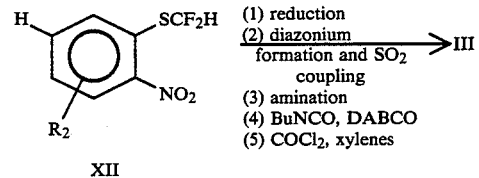

wherein $R_2$ is as previously defined.

Nitro derivatives such as XIII are preferably prepared as shown below in Equation 12 via alkylation of the appropriate thiophenols XIV according to the method of Yagutolskii, et al., *Chemical Abstracts*, 70, 96318d (1969).

EQUATION 12

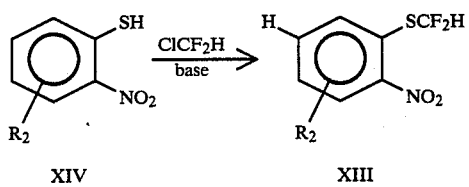

wherein $R_2$ is as previously defined.

The disclosure of all of the above is herein incorporated by reference.

The compounds of this invention and their preparation are further illustrated by the following examples wherein temperatures are given in degrees centigrade and all parts are by weight unless otherwise indicated.

EXAMPLE 1

2-Chloro-4,6-dimethoxy-1,3,5-triazine

To a vigorously-stirred suspension of 54.6 g of sodium bicarbonate in 146 g of methanol and 16 ml water was added 60.0 g of cyanuric chloride in portions over a period of 30 minutes. The temperature rose to 30°–35° C. and, following the addition, was allowed to drop to 25° C. and the mixture was then heated to 50°±2° C. for 2½ hours. The solution was allowed to cool and 600 ml ice-water was added and stirred for 15 minutes. Filtration of the thick reaction mixture followed by crystallization from hot hexanes gave 31.3 g of 2-chloro-4,6-dimethoxy-1,3,5-triazine as a colorless crystalline solid, m.p. 76°–78° C.

NMR(CDCl$_3$): δ, 4.1 (singlet, OCH$_3$'s).

EXAMPLE 2

Trimethyl(4,6-dimethoxy-1,3,5-triazin-2-yl)ammonium chloride

A solution of 25.0 g of the product from Example 1 in 340 ml dry acetone and 140 ml dry tetrahydrofuran was treated at 0° C. with 21.5 ml of liquid trimethylamine, added over a period of 10 minutes. The resulting thick white reaction mixture was stirred at room temperature for 3 hours. Filtration under nitrogen and drying in vacuo gave 30.4 g of trimethyl(4,6-dimethoxy-1,3,5-triazin-2-yl)ammonium chloride as a white powder, m.p. 130°–134° C.

NMR(DMSO-d$_6$+CDCl$_3$): δ 4.2 (6H, s, OCH$_3$'s); 3.7 (9H, s, $^+$N(CH$_3$)$_3$).

EXAMPLE 3

2-Cyano-4,6-dimethoxy-1,3,5-triazine

A mixture of 26 g of potassium cyanide and 60 g of oven-dried acetamide was heated to 85°–90° C. To this melt was added 24 g of the product from Example 2 in portions over a period of 15–20 minutes. The resulting brown reaction solution was heated to 90°–100° C. for an additional one hour. When the solution had cooled to room temperature, water was added and the aqueous layer was extracted with ether and methylene chloride. The combined organic extracts were backwashed with several small portions of water, brine, and were then dried over magnesium sulfate and concentrated in vacuo to afford 6.5 g of 2-cyano-4,6-dimethoxy-1,3,5-triazine as a light yellow solid.

NMR(DMSO-d$_6$+CDCl$_3$): δ 3.9 (singlet, OCH$_3$'s).

EXAMPLE 4

2-Aminomethyl-4,6-dimethoxy-1,3,5-triazine

A mixture of 6.4 g of the product from Example 3, 0.69 g, 10% palladium-on-carbon catalyst, and 3 ml of concentrated hydrochloric acid in 140 ml methanol was shaken under an atmosphere of hydrogen at 50 p.s.i. on a Parr Hydrogenation Apparatus. After approximately 4 hours, the solution was filtered through a pad of Celite and the filtrate was concentrated in vacuo. The residue was diluted with water and, after being washed with several small portions of ether, the aqueous layer was made strongly basic to pH paper by the addition of 50% sodium hydroxide solution with ice-water cooling. A yellow solid precipitated from the basic solution and was isolated by filtration. Drying in vacuo for 24 hours gave 2.4 g of 2-aminomethyl-4,6-dimethoxy-1,3,5-triazine as a light yellow solid.

NMR(DMSO-d$_6$+CDCl$_3$): δ 7.3 (2H, br s, NH$_2$); 3.8 (8H, s, —CH$_2$— and OCH$_3$'s).

EXAMPLE 5

N'[(4,6-Dimethoxy-1,3,5-triazin-2-yl)methylaminocarbonyl]-N,N-dimethyl-1,2-benzenedisulfonamide A solution of 1.3 g of 2-(N,N-dimethylsulfamoyl)-benzenesulfonyl isocyanate in 25 ml of dry acetonitrile was treated at room temperature with 0.58 g of the product from Example 4. The resulting suspension was heated to 50°–55° C. for 1½ hours and was then stirred at room temperature for an additional 15 hours. The solution was filtered and the collected solid washed well with 1-chlorobutane and then dried to yield 0.96 g of N'-[(4,6-dimethoxy-1,3,5-triazin-2-yl)methylaminocarbonyl]-N,N-dimethyl-1,2-benzenedisulfonamide as a light yellow powder, m.p. 183°–189° C., contaminated with some of the unreacted heterocyclic amine. Stirring the crude product with 5% hydrochloric acid at room temperature for 15 minutes followed by filtration gave the pure product as a white powder, m.p. 199°–201° C.

NMR(DMSO-d$_6$+CDCl$_3$): δ 12.3 (1H, br s, NH); 11.0 (1H, br s, NH); 8.4 (1H, m); 8.0 (3H, m); 4.0 (8H, s, —CH$_2$— and heterocyclic OCH$_3$'s); 2.9 (6H, s, SO$_2$N(CH$_3$)$_2$).

IR(KBr): 1710 (c=o), 1600, 1550, 1490, 1460, 1380, 1350 cm$^{-1}$.

EXAMPLE 6

2-Chloro-4-methyl-6-methoxypyrimidine

A solution of 25.4 g of 2amino-4-methyl-6-methoxypyrimidine in 150 ml concentrated hydrochloric acid was cooled to ca. 0° C. and treated with a solution of 25.3 g of sodium nitrite in 50 ml water, added over a period of 30–40 minutes. The thick orange reaction mixture was stirred at room temperature for 4–5 hours and then adjusted to pH 10 by addition of 12.5N sodium hydroxide solution. The precipitate was filtered and extracted thoroughly with approximately 600 ml of hot ether. The organic layer was dried over magnesium sulfate and concentrated in vacuo to give 7.2 g of 2-chloro-4-methyl-6-methoxypyrimidine as a white, crystalline solid, m.p. 36°–38° C.

NMR(CDCl$_3$): δ6.5 (1H, s, heterocyclic H); 4.0 (3H, s, —OCH$_3$); 2.4 (3H, s, —CH$_3$).

EXAMPLE 7

Trimethyl-2-(4-methyl-6-methoxypyrimidinyl)ammonium chloride

A solution of 6.5 g of the product from Example 6 in 100 ml dry acetone was treated at 0° C. with 8 ml of liquid trimethylamine. When the addition was complete (10–15 minutes), the reaction mixture was stirred at room temperature for 15 hours. Filtration of the thick solution followed by drying in vacuo afforded 5.1 g of trimethyl-2-(4-methyl-6-methoxypyrimidinyl)ammonium chloride as a white solid.

NMR(DMSO-d$_6$): δ 7.2 (1H, s, heterocyclic H); 4.0 (3H, s, OCH$_3$); 3.6 (9H, s, $^\oplus$N(CH$_3$)$_3$); 3.1 (3H, s, CH$_3$).

EXAMPLE 8

2-Cyano-4-methyl-6-methoxypyrimidine

A mixture of 25 g of potassium cyanide and 60 g of oven-dried acetamide was heated to 85°–90° C. To this melt was added 8.8 g of the product from Example 7 in portions over a period of 15 minutes. The resulting dark reaction mixture was heated to 90°–100° C. for an additional hour. After the solution had cooled, water was added and the aqueous layer was extracted with ether. The combined organic extracts were backwashed with several small portions of water and brine. Drying and concentrating the ether layer gave 4.7 g of 2-cyano-4-methyl-6-methoxypyrimidine as a yellow solid, m.p. 80°–85° C.

NMR(CDCl$_3$): δ 6.8 (1H, s, heterocyclic H); 4.0 (3H, s, OCH$_3$); 2.5 (3H, s, CH$_3$).

EXAMPLE 9

2-Aminomethyl-4-methyl-6-methoxypyrimidine

A mixture of 4.4 g of the product from Example 8, 0.35 g 10% palladium-on-carbon catalyst, and 1.5 ml of concentrated hydrochloric acid in 70 ml methanol was shaken under an atmosphere of hydrogen at 46 p.s.i. on a Parr Hydrogenation Apparatus. After 3½ hours, the solution was filtered through a pad of Celite and the filtrate was concentrated in vacuo. The resulting solid was taken up in water and the aqueous layer was washed with several small portions of ether. Adjustment to pH 13 followed by extraction with methylene chloride, drying, and evaporation of the organic layer gave 1.8 g of the title compound as a light yellowish-orange oil.

NMR(CDCl$_3$): δ 6.4 (1H, s, heterocyclic H); 3.9 (5H, s, OCH$_3$ and CH$_2$); 2.4 (3H, s, CH$_3$); 1.9 (2H, s, NH$_2$—exchangeable with D$_2$O).

EXAMPLE 10

N'-[(4-Methoxy-6-methylpyrimidin-2-yl)methylaminocarbonyl]-N,N-dimethyl-1,2-benzenedisulfonamide The product from Example 9 (0.90 g) was added in a steady stream to a stirred solution of 2.3 g of 2-(N,N-dimethylsulfamoyl)benzenesulfonyl isocyanate in 20 ml dry methylene chloride at room temperature. The reaction solution was stirred for an additional 18 hours and the solvent was removed in vacuo. The resulting yellow foam was stirred with 1-chlorobutane for ca. one hour. The mixture was filtered and the collected solids dried to yield 1.3 g of N'-[(4-methoxy-6-methylpyrimidin-2-yl)methylaminocarbonyl]-N,N-dimethyl-1,2-benzenedisulfonamide, m.p. 153°–156° C., as a light yellow solid.

NMR(CDCl$_3$+DMSO-d$_6$): δ 8.5 (1H, m); 8.1–7.6 (3H, m); 6.5 (1H, s, heterocyclic H); 4.4 (2H, d, CH$_2$); 3.9 (3H, s, OCH$_3$); 2.9 (6H, s, SO$_2$N(CH$_3$)$_2$); 2.4 (3H, s, CH$_3$).

Using the procedures and examples described above and starting with the appropriate heterocycle and arylsulfonyl isocyanate, the compounds listed in Tables 1 and 2 may be prepared.

TABLE 1

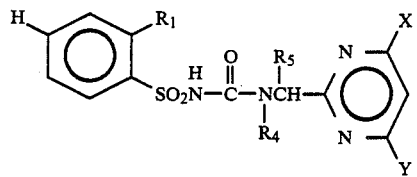

| R$_1$ | R$_4$ | R$_5$ | X | Y | m.p. (°C.) |
|---|---|---|---|---|---|
| NO$_2$ | H | H | OCH$_3$ | CH$_3$ | |
| NO$_2$ | H | H | OCH$_3$ | OCH$_3$ | 147–150° |
| NO$_2$ | H | CH$_3$ | OCH$_3$ | CH$_3$ | |
| Cl | H | H | OCH$_3$ | OCH$_3$ | 95–100°(d) |
| Cl | H | H | CH$_3$ | CH$_3$ | 160–168°(d) |
| Cl | H | H | OCH$_3$ | CH$_3$ | 145–149° |
| F | H | H | OCH$_3$ | CH$_3$ | |
| Br | H | H | OCH$_3$ | CH$_3$ | |
| CF$_3$ | H | H | OCH$_3$ | CH$_3$ | |
| CH$_3$ | H | H | OCH$_3$ | CH$_3$ | |
| CH$_3$ | H | H | OCH$_3$ | OCH$_3$ | 144–146° |
| CH$_2$CH$_3$ | H | H | OCH$_3$ | CH$_3$ | |
| i-Pr | H | H | OCH$_3$ | CH$_3$ | |
| CO$_2$CH$_3$ | H | H | OCH$_3$ | OCH$_3$ | 196–199° |
| CO$_2$CH$_3$ | H | H | OCH$_3$ | CH$_3$ | |
| CO$_2$CH$_3$ | CH$_3$ | H | OCH$_3$ | CH$_3$ | |
| CO$_2$CH$_3$ | H | CH$_3$ | OCH$_3$ | CH$_3$ | |
| CO$_2$CH$_3$ | H | H | CH$_3$ | CH$_3$ | 108–110°(d) |
| CO$_2$CH$_2$CH$_3$ | H | H | OCH$_3$ | CH$_3$ | |
| CO$_2$—i-Pr | H | H | OCH$_3$ | CH$_3$ | |
| CO$_2$CH$_2$CH=CH$_2$ | H | H | OCH$_3$ | CH$_3$ | |
| CO$_2$CH$_2$CH$_2$Cl | H | H | OCH$_3$ | CH$_3$ | |
| CO$_2$CH$_2$CH$_2$OCH$_3$ | H | H | OCH$_3$ | CH$_3$ | |
| SCH$_3$ | H | H | OCH$_3$ | CH$_3$ | |
| SCH$_2$CH$_3$ | H | H | OCH$_3$ | CH$_3$ | |
| S—i-Pr | H | H | OCH$_3$ | CH$_3$ | |
| SCH$_2$CH=CH$_2$ | H | H | OCH$_3$ | CH$_3$ | |
| SO$_2$CH$_3$ | H | H | OCH$_3$ | OCH$_3$ | 222–224° |
| SO$_2$CH$_3$ | H | H | OCH$_3$ | CH$_3$ | |
| SO$_2$CH$_2$CH$_3$ | H | H | OCH$_3$ | CH$_3$ | |
| SO$_2$—i-Pr | H | H | OCH$_3$ | CH$_3$ | |
| SO$_2$CH$_2$CH=CH$_2$ | H | H | OCH$_3$ | CH$_3$ | |
| SO$_2$N(CH$_3$)$_2$ | H | H | OCH$_3$ | OCH$_3$ | 143–147° |
| SO$_2$N(CH$_3$)$_2$ | H | H | OCH$_3$ | CH$_3$ | 153–156° |
| SO$_2$N(CH$_3$)$_2$ | H | H | CH$_3$ | CH$_3$ | 166–169° |
| SO$_2$N(CH$_3$)$_2$ | H | H | CH$_3$ | Et | |
| SO$_2$N(CH$_3$)$_2$ | H | H | CH$_3$ | OEt | |
| SO$_2$N(CH$_3$)$_2$ | H | H | CH$_3$ | CH$_2$OCH$_3$ | |
| SO$_2$N(CH$_3$)$_2$ | H | H | CH$_3$ | CH(OCH$_3$)$_2$ | |

TABLE 1-continued

Structure: H-phenyl(R₁)-SO₂N(H)-C(O)-N(R₄)-CH(R₅)-pyrimidine(X,Y)

| R₁ | R₄ | R₅ | X | Y | m.p. (°C.) |
|---|---|---|---|---|---|
| SO₂N(CH₃)₂ | H | H | CH₃ | (1,3-dioxolan-2-yl CH) | |
| SO₂N(CH₃)₂ | CH₃ | H | OCH₃ | CH₃ | |
| SO₂N(CH₃)₂ | H | CH₃ | OCH₃ | CH₃ | |
| SO₂N(CH₃)Et | H | H | OCH₃ | CH₃ | |
| SO₂N(CH₃)iPr | H | H | OCH₃ | CH₃ | |
| OSO₂CH₃ | H | H | OCH₃ | OCH₃ | 167–171° |
| OSO₂CH₃ | H | H | OCH₃ | CH₃ | |
| OSO₂CH₃ | H | H | CH₃ | CH₃ | 186–188°(d) |
| OSO₂Et | H | H | OCH₃ | CH₃ | |
| OSO₂iPr | H | H | OCH₃ | CH₃ | |
| OCH₃ | H | H | OCH₃ | OCH₃ | |
| OCH₃ | H | H | OCH₃ | CH₃ | |
| OCH₃ | H | H | CH₃ | CH₃ | |
| OCH₂CH₃ | H | H | OCH₃ | CH₃ | |
| O-nPr | H | H | CH₃ | CH₃ | 152–155° |
| O-iPr | H | H | OCH₃ | CH₃ | |
| OCH₂CH₂OCH₃ | H | H | OCH₃ | CH₃ | |
| SO₂-nPr | H | H | OCH₃ | OCH₃ | |
| OCF₂H | H | H | OCH₃ | OCH₃ | |
| OCF₂H | H | H | CH₃ | OCH₃ | |
| SCF₂H | H | H | CH₃ | OCH₃ | |
| SCF₂H | H | H | OCH₃ | OCH₃ | |
| CH₂CH₂OCH₃ | H | H | OCH₃ | OCH₃ | |
| (1,3,4-oxadiazol-2-yl) | H | H | OCH₃ | OCH₃ | |
| (5-methyl-1,3,4-oxadiazol-2-yl) | H | H | CH₃ | OCH₃ | |
| (isoxazol-3-yl) | H | H | OCH₃ | OCH₃ | |
| (isoxazol-5-yl) | H | H | OCH₃ | OCH₃ | |
| (1,2,3-thiadiazol-4-yl) | H | H | OCH₃ | OCH₃ | |

TABLE 2

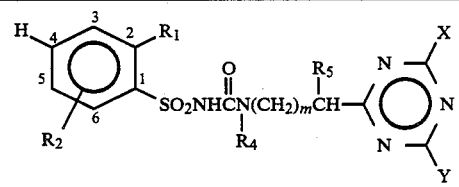

| R₁ | R₂ | R₄ | R₅ | m | X | Y | m.p. (°C.) |
|---|---|---|---|---|---|---|---|
| NO₂ | H | H | H | 0 | OCH₃ | OCH₃ | 190–192° |
| NO₂ | H | H | H | 0 | OCH₃ | CH₃ | |
| NO₂ | H | H | H | 0 | CH₃ | CH₃ | |
| NO₂ | H | H | CH₃ | 0 | OCH₃ | CH₃ | |
| NO₂ | 6-Cl | H | H | 0 | OCH₃ | CH₃ | |
| NO₂ | 5-Cl | H | H | 0 | OCH₃ | CH₃ | |
| NO₂ | 5-CF₃ | H | H | 0 | OCH₃ | CH₃ | |
| Cl | H | H | H | 0 | OCH₃ | CH₃ | |
| Cl | H | H | H | 0 | OCH₃ | OCH₃ | 169–171° |
| Cl | H | H | H | 0 | CH₃ | CH₃ | |
| Cl | 5-CH₃ | H | H | 0 | OCH₃ | CH₃ | |
| Cl | 3-Br | H | H | 0 | OCH₃ | CH₃ | |
| F | 6-F | H | H | 0 | OCH₃ | CH₃ | |
| Br | 3-F | H | H | 0 | OCH₃ | CH₃ | |
| CF₃ | H | H | H | 0 | OCH₃ | CH₃ | |
| CH₃ | H | H | H | 0 | OCH₃ | CH₃ | |
| CH₃ | H | H | H | 0 | OCH₃ | OCH₃ | |

TABLE 2-continued

Structure: benzene ring with H at position 4, R₁ at position 2, R₂ at position 6, and at position 1: SO₂NHC(O)N(R₄)(CH₂)ₘCH(R₅)-[pyrimidine with X and Y substituents]

| R₁ | R₂ | R₄ | R₅ | m | X | Y | m.p. (°C.) |
|---|---|---|---|---|---|---|---|
| CH₃ | H | H | H | 0 | CH₃ | CH₃ | |
| CH₃ | 6-CH₃ | H | H | 0 | OCH₃ | CH₃ | |
| CH₃ | 6-OCH₃ | H | H | 0 | OCH₃ | CH₃ | |
| CH₂CH₃ | H | H | H | 0 | OCH₃ | CH₃ | |
| i-Pr | H | H | H | 0 | OCH₃ | CH₃ | |
| CO₂CH₃ | H | H | H | 0 | OCH₃ | OCH₃ | 183–185° |
| CO₂CH₃ | H | H | H | 0 | OCH₃ | CH₃ | |
| CO₂CH₃ | H | CH₃ | H | 0 | OCH₃ | CH₃ | |
| CO₂CH₃ | H | H | CH₃ | 0 | OCH₃ | CH₃ | |
| CO₂CH₃ | 3-CF₃ | H | H | 0 | OCH₃ | CH₃ | |
| CO₂CH₃ | 4-OCH₃ | H | H | 0 | OCH₃ | CH₃ | |
| CO₂CH₃ | 5-CH₃ | H | H | 0 | OCH₃ | CH₃ | |
| CO₂CH₃ | 6-CH₃ | H | H | 0 | OCH₃ | CH₃ | |
| CO₂CH₂CH₃ | H | H | H | 0 | OCH₃ | OCH₃ | |
| CO₂-i-Pr | H | H | H | 0 | OCH₃ | OCH₃ | |
| CO₂CH₂CH=CH₂ | H | H | H | 0 | OCH₃ | CH₃ | |
| CO₂CH₂CH₂Cl | H | H | H | 0 | OCH₃ | CH₃ | |
| CO₂CH₂CH₂OCH₃ | H | H | H | 0 | OCH₃ | CH₃ | |
| SCH₃ | H | H | H | 0 | OCH₃ | CH₃ | |
| SCH₂CH₃ | H | H | H | 0 | OCH₃ | CH₃ | |
| S-i-Pr | H | H | H | 0 | OCH₃ | CH₃ | |
| SCH₂CH=CH₂ | H | H | H | 0 | OCH₃ | CH₃ | |
| SO₂CH₃ | H | H | H | 0 | OCH₃ | OCH₃ | |
| SO₂CH₃ | H | H | H | 0 | OCH₃ | CH₃ | |
| SO₂CH₃ | H | H | H | 0 | CH₃ | CH₃ | |
| SO₂CH₃ | 4-OCH₃ | H | H | 0 | OCH₃ | CH₃ | |
| SO₂CH₃ | 5-CF₃ | H | H | 0 | OCH₃ | CH₃ | |
| SO₂CH₂CH₃ | H | H | H | 0 | OCH₃ | CH₃ | |
| SO₂-i-Pr | H | H | H | 0 | OCH₃ | CH₃ | |
| SO₂CH₂CH=CH₂ | H | H | H | 0 | OCH₃ | CH₃ | |
| SO₂N(CH₃)₂ | H | H | H | 0 | OCH₃ | OCH₃ | 199–201° |
| SO₂N(CH₃)₂ | H | H | H | 0 | OCH₃ | CH₃ | |
| SO₂N(CH₃)₂ | H | H | H | 0 | CH₃ | CH₃ | |
| SO₂N(CH₃)₂ | H | H | H | 0 | CH₃ | Et | |
| SO₂N(CH₃)₂ | H | H | H | 0 | CH₃ | OEt | |
| SO₂N(CH₃)₂ | H | H | H | 0 | CH₃ | CH₂OCH₃ | |
| SO₂N(CH₃)₂ | H | H | H | 0 | CH₃ | CH(OCH₃)₂ | |
| SO₂N(CH₃)₂ | H | H | H | 0 | CH₃ | CH(OCH₂CH₂O) (1,3-dioxolan-2-yl) | |
| SO₂N(CH₃)₂ | H | CH₃ | H | 0 | OCH₃ | CH₃ | |
| SO₂N(CH₃)₂ | H | H | CH₃ | 0 | OCH₃ | CH₃ | |
| SO₂N(CH₃)₂ | 5-Cl | H | H | 0 | OCH₃ | CH₃ | |
| SO₂N(CH₃)Et | H | H | H | 0 | OCH₃ | CH₃ | |

TABLE 2-continued

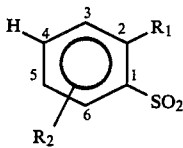

| R₁ | R₂ | R₄ | R₅ | m | X | Y | m.p. (°C.) |
|---|---|---|---|---|---|---|---|
| SO₂N(CH₃)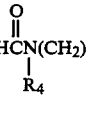 | H | H | H | 0 | OCH₃ | CH₃ | |
| OSO₂CH₃ | H | H | H | 0 | OCH₃ | OCH₃ | |
| OSO₂CH₃ | H | H | H | 0 | OCH₃ | CH₃ | |
| OSO₂CH₃ | H | H | H | 0 | CH₃ | CH₃ | |
| OSO₂Et | H | H | H | 0 | OCH₃ | CH₃ | |
| OSO₂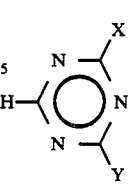 | H | H | H | 0 | OCH₃ | CH₃ | |
| OCH₃ | H | H | H | 0 | OCH₃ | OCH₃ | |
| OCH₃ | H | H | H | 0 | OCH₃ | CH₃ | |
| OCH₃ | H | H | H | 0 | CH₃ | CH₃ | |
| OCH₃ | 6-OCH₃ | H | H | 0 | OCH₃ | CH₃ | |
| OCH₃ | 6-CH₃ | H | H | 0 | OCH₃ | CH₃ | |
| OCH₂CH₃ | H | H | H | 0 | OCH₃ | CH₃ | |
| O | H | H | H | 0 | OCH₃ | CH₃ | |
| OOCH₃ | H | H | H | 0 | OCH₃ | CH₃ | |
| SO₂ | H | H | H | 0 | OCH₃ | OCH₃ | |
| SO₂CH₃ | 5-CF₃ | H | H | 0 | OCH₃ | OCH₃ | |
| SO₂N(CH₃)₂ | 5-CF₃ | H | H | 0 | OCH₃ | OCH₃ | |
| SO₂N(CH₃)₂ | H | H | H | 1 | OCH₃ | OCH₃ | |
| SO₂N(CH₃)₂ | H | H | H | 1 | OCH₃ | CH₃ | |
| SO₂N(CH₃)₂ | H | CH₃ | H | 1 | OCH₃ | OCH₃ | |
| SO₂N(CH₃)₂ | H | H | CH₃ | 1 | OCH₃ | OCH₃ | |
| OCF₂H | H | H | H | 0 | OCH₃ | OCH₃ | |
| SCF₂H | H | H | H | 0 | OCH₃ | OCH₃ | |
| CH₂CH₂OCH₃ | H | H | H | 0 | OCH₃ | OCH₃ | |
|  | H | H | H | 0 | OCH₃ | OCH₃ | |
|  | H | H | H | 0 | OCH₃ | OCH₃ | |
|  | H | H | H | 0 | OCH₃ | OCH₃ | |
|  | H | H | H | 0 | OCH₃ | OCH₃ | |
|  | H | H | H | 0 | OCH₃ | OCH₃ | |
| —SO₂N—OCH₃<br>　　　│<br>　　　CH₃ | H | H | H | 0 | OCH₃ | OCH₃ | |

TABLE 2-continued

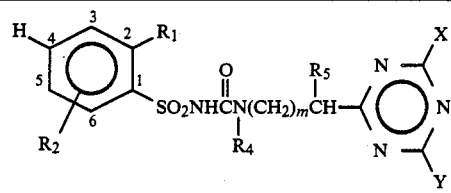

| R₁ | R₂ | R₄ | R₅ | m | X | Y | m.p. (°C.) |
|---|---|---|---|---|---|---|---|
| —CH₂OCH₃ | H | H | H | 0 | OCH₃ | OCH₃ | |
| —CH₂OCH₂CH₃ | H | H | H | 0 | OCH₃ | OCH₃ | |

TABLE 3

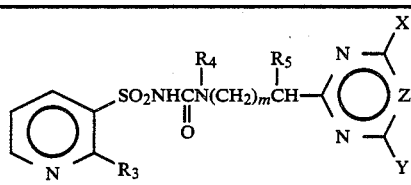

| R₃ | m | R₄ | R₅ | X | Y | Z | m.p. (C) |
|---|---|---|---|---|---|---|---|
| Cl | 0 | H | H | OCH₃ | OCH₃ | CH | |
| Cl | 0 | H | H | OCH₃ | CH₃ | CH | |
| Cl | 0 | H | H | OCH₃ | OCH₃ | N | |
| Cl | 1 | H | H | OCH₃ | OCH₃ | N | |
| Cl | 1 | CH₃ | H | OCH₃ | OCH₃ | N | |
| Cl | 1 | H | CH₃ | OCH₃ | OCH₃ | N | |
| Cl | 1 | CH₃ | H | OCH₃ | OCH₃ | N | |
| Cl | 0 | H | CH₃ | OCH₃ | OCH₃ | N | |
| Cl | 0 | H | H | CH₃ | Et | CH | |
| Cl | 0 | H | H | CH₃ | OEt | CH | |
| Cl | 0 | H | H | CH₃ | CH₂OCH₃ | CH | |
| Cl | 0 | H | H | CH₃ | CH(OCH₃)₂ | CH | |
| Cl | 0 | H | H | CH₃ |  | CH | |
| Cl | 0 | H | H | OCH₃ | Et | N | |
| Cl | 0 | H | H | OCH₃ | OEt | N | |
| Cl | 0 | H | H | OCH₃ | CH₂OCH₃ | N | |
| Cl | 0 | H | H | OCH₃ | CH(OCH₃)₂ | N | |
| Cl | 0 | H | H | OCH₃ |  | N | |
| SO₂CH₃ | 0 | H | H | OCH₃ | OCH₃ | CH | |
| SO₂CH₃ | 0 | H | H | OCH₃ | CH₃ | CH | |
| SO₂CH₃ | 0 | H | H | OCH₃ | OCH₃ | N | |
| SO₂CH₃ | 1 | H | H | OCH₃ | OCH₃ | N | |
| SO₂CH₃ | 1 | CH₃ | H | OCH₃ | OCH₃ | N | |
| SO₂CH₃ | 1 | H | CH₃ | OCH₃ | OCH₃ | N | |
| SO₂CH₃ | 1 | CH₃ | H | OCH₃ | OCH₃ | N | |
| SO₂CH₃ | 0 | H | CH₃ | OCH₃ | OCH₃ | N | |
| SO₂CH₃ | 0 | H | H | CH₃ | Et | CH | |
| SO₂CH₃ | 0 | H | H | CH₃ | OEt | CH | |
| SO₂CH₃ | 0 | H | H | CH₃ | CH₂OCH₃ | CH | |
| SO₂CH₃ | 0 | H | H | CH₃ | CH(OCH₃)₂ | CH | |
| SO₂CH₃ | 0 | H | H | CH₃ |  | CH | |
| SO₂CH₃ | 0 | H | H | OCH₃ | Et | N | |
| SO₂CH₃ | 0 | H | H | OCH₃ | OEt | N | |
| SO₂CH₃ | 0 | H | H | OCH₃ | CH₂OCH₃ | N | |
| SO₂CH₃ | 0 | H | H | OCH₃ | CH(OCH₃)₂ | N | |
| SO₂CH₃ | 0 | H | H | OCH₃ |  | N | |
| SO₂N(CH₃)₂ | 0 | H | H | OCH₃ | OCH₃ | CH | |
| SO₂N(CH₃)₂ | 0 | H | H | OCH₃ | CH₃ | CH | |

TABLE 3-continued

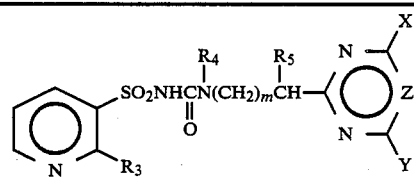

| R₃ | m | R₄ | R₅ | X | Y | Z | m.p. (C) |
|---|---|---|---|---|---|---|---|
| SO₂N(CH₃)₂ | 0 | H | H | OCH₃ | OCH₃ | N | |
| SO₂N(CH₃)₂ | 1 | H | H | OCH₃ | OCH₃ | N | |
| SO₂N(CH₃)₂ | 1 | CH₃ | H | OCH₃ | OCH₃ | N | |
| SO₂N(CH₃)₂ | 1 | H | CH₃ | OCH₃ | OCH₃ | N | |
| SO₂N(CH₃)₂ | 0 | CH₃ | H | OCH₃ | OCH₃ | N | |
| SO₂N(CH₃)₂ | 0 | H | CH₃ | OCH₃ | OCH₃ | N | |
| SO₂N(CH₃)₂ | 0 | H | H | CH₃ | Et | CH | |
| SO₂N(CH₃)₂ | 0 | H | H | CH₃ | OEt | CH | |
| SO₂N(CH₃)₂ | 0 | H | H | CH₃ | CH₂OCH₃ | CH | |
| SO₂N(CH₃)₂ | 0 | H | H | CH₃ | CH(OCH₃)₂ | CH | |
| SO₂N(CH₃)₂ | 0 | H | H | CH₃ |  | CH | |
| SO₂N(CH₃)₂ | 0 | H | H | OCH₃ | Et | N | |
| SO₂N(CH₃)₂ | 0 | H | H | OCH₃ | OEt | N | |
| SO₂N(CH₃)₂ | 0 | H | H | OCH₃ | CH₂OCH₃ | N | |
| SO₂N(CH₃)₂ | 0 | H | H | OCH₃ | CH(OCH₃)₂ | N | |
| SO₂N(CH₃)₂ | 0 | H | H | OCH₃ |  | N | |

TABLE 4

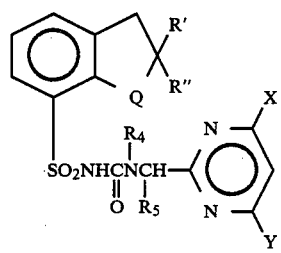

| Q | R' | R'' | R₄ | R₅ | X | Y | m.p. (C.) |
|---|---|---|---|---|---|---|---|
| O | H | H | H | H | OCH₃ | OCH₃ | |
| O | H | H | H | H | OCH₃ | CH₃ | |
| O | H | H | CH₃ | H | OCH₃ | CH₃ | |
| O | H | H | H | CH₃ | OCH₃ | CH₃ | |
| O | CH₃ | H | H | H | OCH₃ | CH₃ | |
| O | CH₃ | CH₃ | H | H | OCH₃ | CH₃ | |
| O | H | CH₂CH₃ | H | H | OCH₃ | CH₃ | |

TABLE 4-continued

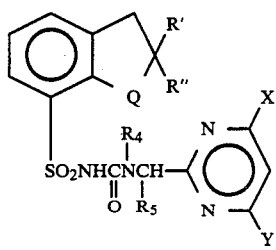

| Q | R' | R" | R4 | R5 | X | Y m.p. (C.) |
|---|----|----|----|----|----|----|
| O | H |  ⊰  | H | H | OCH3 | CH3 |
| O | H | H | H | H | CH3 | Et |
| O | H | H | H | H | CH3 | OEt |
| O | H | H | H | H | CH3 | CH2OCH3 |
| O | H | H | H | H | CH3 | CH(OCH3)2 |
| O | H | H | H | H | CH3 | (dioxolane) |
| S | H | H | H | H | OCH3 | OCH3 |
| S | H | H | H | H | OCH3 | CH3 |
| S | H | H | CH3 | H | OCH3 | CH3 |
| S | H | H | H | CH3 | OCH3 | CH3 |
| S | CH3 | H | H | H | OCH3 | CH3 |
| S | CH3 | CH3 | H | H | OCH3 | CH3 |
| S | H | CH2CH3 | H | H | OCH3 | CH3 |
| S | H | ⊰ | H | H | OCH3 | CH3 |
| S | H | H | H | H | CH3 | Et |
| S | H | H | H | H | CH3 | OEt |
| S | H | H | H | H | CH3 | CH2OCH3 |
| S | H | H | H | H | CH3 | CH(OCH3)2 |
| S | H | H | H | H | CH3 | (dioxolane) |
| SO2 | H | H | H | H | OCH3 | OCH3 |
| SO2 | H | H | H | H | OCH3 | CH3 |
| SO2 | H | H | CH3 | H | OCH3 | CH3 |
| SO2 | H | H | H | CH3 | OCH3 | CH3 |
| SO2 | CH3 | H | H | H | OCH3 | CH3 |
| SO2 | CH3 | CH3 | H | H | OCH3 | CH3 |
| SO2 | H | CH2CH3 | H | H | OCH3 | CH3 |
| SO2 | H | ⊰ | H | H | OCH3 | CH3 |
| SO2 | H | H | H | H | CH3 | Et |
| SO2 | H | H | H | H | CH3 | OEt |
| SO2 | H | H | H | H | CH3 | CH2OCH3 |
| SO2 | H | H | H | H | CH3 | CH(OCH3)2 |
| SO2 | H | H | H | H | CH3 | (dioxolane) |

TABLE 5

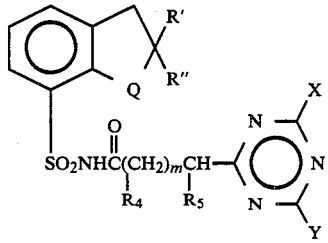

| Q | R' | R" | m | R4 | R5 | X | Y m.p. (C.) |
|---|----|----|----|----|----|----|----|
| O | H | H | 0 | H | H | OCH3 | OCH3 |
| O | H | H | 0 | H | H | OCH3 | CH3 |
| O | H | H | 0 | CH3 | H | OCH3 | CH3 |
| O | H | H | 0 | H | CH3 | OCH3 | CH3 |
| O | CH3 | H | 0 | H | H | OCH3 | CH3 |
| O | CH3 | CH3 | 0 | H | H | OCH3 | CH3 |
| O | H | CH2CH3 | 0 | H | H | OCH3 | CH3 |
| O | H | ⊰ | 0 | H | H | OCH3 | CH3 |
| O | H | H | 0 | H | H | CH3 | Et |
| O | H | H | 0 | H | H | CH3 | OEt |
| O | H | H | 0 | H | H | CH3 | CH2OCH3 |
| O | H | H | 0 | H | H | CH3 | CH(OCH3)2 |
| O | H | H | 0 | H | H | CH3 | (dioxolane) |
| O | H | H | 1 | H | H | OCH3 | OCH3 |
| O | H | H | 1 | CH3 | H | OCH3 | OCH3 |
| O | H | H | 1 | H | CH3 | OCH3 | OCH3 |
| S | H | H | 0 | H | H | OCH3 | OCH3 |
| S | H | H | 0 | H | H | OCH3 | CH3 |
| S | H | H | 0 | CH3 | H | OCH3 | CH3 |
| S | H | H | 0 | H | CH3 | OCH3 | CH3 |
| S | CH3 | H | 0 | H | H | OCH3 | CH3 |
| S | CH3 | CH3 | 0 | H | H | OCH3 | CH3 |
| S | H | CH2CH3 | 0 | H | H | OCH3 | CH3 |
| S | H | H | 0 | H | H | OCH3 | CH3 |
| S | H | H | 0 | H | H | CH3 | Et |
| S | H | H | 0 | H | H | CH3 | OEt |
| S | H | H | 0 | H | H | CH3 | CH2OCH3 |
| S | H | H | 0 | H | H | CH3 | CH(OCH3)2 |
| S | H | H | 0 | H | H | CH3 | (dioxolane) |
| S | H | H | 1 | H | H | OCH3 | OCH3 |
| S | H | H | 1 | CH3 | H | OCH3 | OCH3 |
| S | H | H | 1 | H | CH3 | OCH3 | OCH3 |
| SO2 | H | H | 0 | H | H | OCH3 | OCH3 |
| SO2 | H | H | 0 | H | H | OCH3 | CH3 |
| SO2 | H | H | 0 | CH3 | H | OCH3 | CH3 |
| SO2 | H | H | 0 | H | CH3 | OCH3 | CH3 |
| SO2 | CH3 | H | 0 | H | H | OCH3 | CH3 |
| SO2 | CH3 | CH3 | 0 | H | H | OCH3 | CH3 |
| SO2 | H | CH2CH3 | 0 | H | H | OCH3 | CH3 |
| SO2 | H | H | 0 | H | H | OCH3 | CH3 |
| SO2 | H | H | 0 | H | H | CH3 | Et |
| SO2 | H | H | 0 | H | H | CH3 | OEt |
| SO2 | H | H | 0 | H | H | CH3 | CH2OCH3 |
| SO2 | H | H | 0 | H | H | CH3 | CH(OCH3)2 |
| SO2 | H | H | 0 | H | H | CH3 | (dioxolane) |
| SO2 | H | H | 1 | H | H | OCH3 | OCH3 |
| SO2 | H | H | 1 | CH3 | H | OCH3 | OCH3 |

TABLE 5-continued

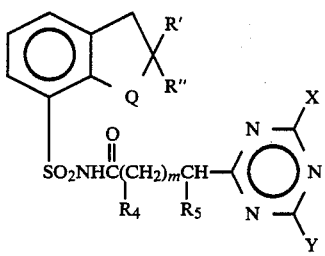

| Q | R' | R" | m | R$_4$ | R$_5$ | X | Y | m.p. (C.) |
|---|----|----|---|------|------|----|----|-----------|
| SO$_2$ | H | H | 1 | H | CH$_3$ | OCH$_3$ | OCH$_3$ | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert dilutent(s). More specifically, they will contain these ingredients in the following approximate proportions:

TABLE 6

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

In the following examples, all parts are by weight unless otherwise indicated.

EXAMPLE 11

Wettable Powder

| | |
|---|---|
| Methyl 2-[N—[(4,6-dimethoxypyrimidin-2-yl)methylaminocarbonyl]aminosulfonyl]benzoate | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 12

Wettable Powder

| | |
|---|---|
| N'—[(4,6-Dimethylpyrimidin-2-yl)methylaminocarbonyl]-N,N—dimethyl-1,2-benzenedisulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 13

Granule

| | |
|---|---|
| Wettable Powder of Example 12 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 14

Extruded Pellet

| | |
|---|---|
| N'—[(4,6-Dimethoxy-1,3,5-triazin-2-yl)methylaminocarbonyl]-N,N—dimethyl-1,2-benzenedisulfonamide | 25% |
| anhydrous sodium sulfate | 10% |
| crude calcium ligninsulfonate | 5% |
| sodium alkylnaphthalenesulfonate | 1% |

| | |
|---|---|
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 15

Oil Suspension

| | |
|---|---|
| N'—[(4,6-Dimethoxypyrimidin-2-yl)methylaminocarbonyl]-N,N—dimethyl-1,2-benzenedisulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 16

Wettable Powder

| | |
|---|---|
| N'—[(4,6-Dimethoxy-1,3,5-triazin-2-yl)methylaminocarbonyl]-N,N—dimethyl-1,2-benzenedisulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 17

Low Strength Granule

| | |
|---|---|
| N'—[(4,6-Dimethoxy-1,3,5-triazin-2-yl)methylaminocarbonyl]-N,N—dimethyl-1,2-benzenedisulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 18

Aqueous Suspension

| | |
|---|---|
| N'—[(4-Methoxy-6-methylpyrimidin-2-yl)methylaminocarbonyl]-N,N—dimethyl-1,2-benzenedisulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 19

Solution

| | |
|---|---|
| N'—[(4,6-Dimethoxypyrimidin-2-yl)methylaminocarbonyl]-N,N—dimethyl-1,2-benzenedisulfonamide, sodium salt | 5% |
| water | 95% |

The salt is added directly to the water with stirring to produce the solution, which may then be packaged for use.

EXAMPLE 20

Low Strength Granule

| | |
|---|---|
| N'—[(4-Methoxy-6-methylpyrimidin-2-yl)methylaminocarbonyl]-N,N—dimethyl-1,2-benzenedisulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 21

Granule

| | |
|---|---|
| Methyl 2-[N—[(4,6-dimethoxypyrimidin-2-yl)methylaminocarbonyl]aminosulfonyl]benzoate | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and pacakaged for use.

EXAMPLE 22

High Strength Concentrate

| | |
|---|---|
| N'—[(4,6-Dimethoxy-1,3,5-triazin-2-yl)methylaminocarbonyl]-N,N—dimethyl-1,2-benzenedisulfonamide | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

EXAMPLE 23

Wettable Powder

| | |
|---|---|
| Methyl 2-[N—[(4,6-dimethoxypyrimidin-2-yl)methylaminocarbonyl]aminosulfonyl]benzoate | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 24

Wettable Powder

| | |
|---|---|
| N'—[(4,6-Dimethylpyrimidin-2-yl)methylaminocarbonyl]-N,N—dimethyl-1,2-benzenedisulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 25

Oil Suspension

| | |
|---|---|
| N'—[(4-Methoxy-6-methylpyrimidin-2-yl)methylaminocarbonyl]-N,N—dimethyl-1,2-benzenedisulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

UTILITY

The compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for plant growth modification, such as growth retardation or for selective weed control in crops such as wheat.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (*Digitaria* sp.), barnyardgrass (*Echinochloa crusgalli*), wild oats (*Avena fatua*), cassia (*Cassia obtusfolia*), morningglory (*Ipomoea* sp.), cocklebur (*Xanthium* sp.), sorghum, corn, soybean, rice, wheat, nutsedge tubers (*Cyperus rotundus*), and, sometimes, sugar beets were planted in a growth medium and treated pre-emergence with the chemicals dissolved in a non-phytotoxic solvent. At the same time cotton having five leaves (including cotyledonary ones), bush beans with the third trifoliolate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, nutsedge with three to five leaves and, in some instances, sugar beets were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following means:

C=chlorosis/necrosis;
E=emergence inhibition;
G=growth retardation;
H=formative effects;
X=axillary stimulation; and
6Y=abscised buds or flowers.

The ratings for the compounds tested by this procedure are presented in Table A.

Compounds

Compound 1

[Chemical structure: 2-chlorobenzene with SO$_2$NHCNHCH$_2$- (C=O) group connected to 4,6-dimethylpyrimidin-2-yl]

| | |
|---|---|
| Compound 2 | 2-Cl-C6H4-SO2NHC(O)NHCH2-(4-CH3, 6-OCH3-pyrimidin-2-yl) |
| Compound 3 | 2-Cl-C6H4-SO2NHC(O)NHCH2-(4,6-di-OCH3-pyrimidin-2-yl) |
| Compound 4 | 2-SO2N(CH3)2-C6H4-SO2NHC(O)NHCH2-(4,6-di-CH3-pyrimidin-2-yl) |
| Compound 5 | 2-SO2N(CH3)2-C6H4-SO2NHC(O)NHCH2-(4-CH3, 6-OCH3-pyrimidin-2-yl) |
| Compound 6 | 2-SO2N(CH3)2-C6H4-SO2NHC(O)NHCH2-(4,6-di-OCH3-pyrimidin-2-yl) |
| Compound 7 | 2-SO2N(CH3)2-C6H4-SO2NHC(O)NHCH2-(4,6-di-OCH3-1,3,5-triazin-2-yl) |
| Compound 8 | 2-CO2CH3-C6H4-SO2NHC(O)NHCH2-(4,6-di-OCH3-pyrimidin-2-yl) |
| Compound 9 | 2-COOCH3-C6H4-SO2NHC(O)NHCH2-(4,6-di-OCH3-1,3,5-triazin-2-yl) |
| Compound 10 | 2-Cl-C6H4-SO2NHC(O)NHCH2-(4,6-di-OCH3-1,3,5-triazin-2-yl) |
| Compound 11 | 2-NO2-C6H4-SO2NHC(O)NHCH2-(4,6-di-OCH3-1,3,5-triazin-2-yl) |
| Compound 12 | 2-COOCH3-C6H4-SO2NHC(O)NHCH2-(4,6-di-CH3-pyrimidin-2-yl) |
| Compound 13 | 2-OSO2CH3-C6H4-SO2NHC(O)NHCH2-(4,6-di-CH3-pyrimidin-2-yl) |
| Compound 14 | 2-SO2CH2CH2CH3-C6H4-SO2NHC(O)NHCH2-(4,6-di-CH3-pyrimidin-2-yl) |
| Compound 15 | 2-OCH2CH2CH3-C6H4-SO2NHC(O)NHCH2-(4,6-di-CH3-pyrimidin-2-yl) |
| Compound 16 | 2-NO2-C6H4-SO2NHC(O)NHCH2-(4,6-di-OCH3-pyrimidin-2-yl) |
| Compound 17 | 2-SO2CH3-C6H4-SO2NHC(O)NHCH2-(4,6-di-OCH3-pyrimidin-2-yl) |
| Compound 18 | 2,6-di-Cl-C6H3-SO2NHC(O)NHCH2-(4,6-di-OCH3-pyrimidin-2-yl) |

-continued

Compounds

Compound 19

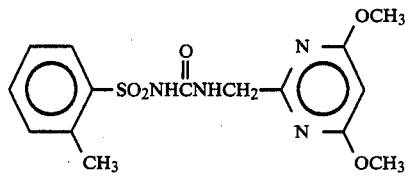

Compound 20

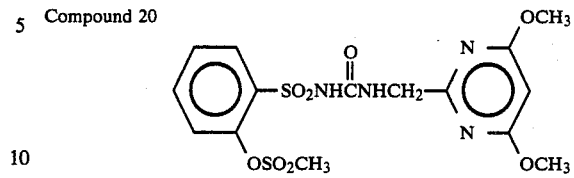

TABLE A

| | Cmpd. 1 | | Cmpd. 2 | | | Cmpd. 3 | | Cmpd. 4 | | Cmpd. 5 | | Cmpd. 6 | |
|---|---|---|---|---|---|---|---|---|---|---|---|---|---|
| Rate kg/ha | 0.4 | 10 | 0.05 | 0.4 | 10 | 0.05 | 0.4 | 0.4 | 0.05 | 0.4 | 0.05 | 0.4 | |
| | | | | | POST-EMERGENCE | | | | | | | | |
| Bush bean | 0 | 0 | 0 | 0 | 2C,3G | 6C,9G,6Y | 9C | 6C,9G | 5C,9G,6Y | 5C,9G,6Y | 4C,9G,6Y | 9C | |
| Cotton | 0 | 0 | 0 | 0 | 3C | — | — | 5C,9G | 4C,8H | 5C,9G | 5C,9G | 5C | |
| Morningglory | 0 | 0 | 0 | 0 | 2C,8G | 2C,8H | 10C | 6C,9G | 4C | 4C,6G | 4C,9G | 10C | |
| Cocklebur | 0 | 0 | 0 | 3G | 3G | 0 | 0 | 5C,9G | 4C,6G | 6C,9G | 4C,8G | 5C,9G | |
| Cassia | 0 | 0 | 0 | 0 | 2C,3G | 5C,9G | 10C | 3C | 2C | 2C | 2C,3G | 9C | |
| Nutsedge | 0 | 0 | 0 | 0 | 0 | 9G | 6C,9G | 1C,5G | 3G | 0 | 5G | 2C,8G | |
| Crabgrass | 0 | 0 | 0 | 0 | 2G | 4G | 1C,5G | 3C,8G | 2G | 4G | 4G | 4C,8G | |
| Barnyardgrass | 0 | 0 | 0 | 0 | 2C,8H | 2C,5H | 4C,8H | 5C,9H | 0 | 1C,4H | 8H | 3C,9H | |
| Wild Oats | 0 | 0 | 0 | 0 | 1C | 0 | 0 | 3C,8G | 0 | 0 | 2G | 8G | |
| Wheat | 0 | 0 | 0 | 0 | 0 | 0 | 0 | 2C,8G | 0 | 0 | 6G | 4C,9G | |
| Corn | 0 | 0 | 0 | 0 | 2C,9H | 2C | 2C,7H | 2C,6H | 1C | 1C | 3G | 9G | |
| Soybean | 0 | 0 | 0 | 0 | 1C,4G | 2C,8G | 9C | 9C | 2H | 2C,7H | 4C,8G,5X | 6C,9G | |
| Rice | 0 | 0 | 0 | 0 | 9G | 6G | 2C,8G | 9C | 4G | 4C,9G | 9G | 5C,9G | |
| Sorghum | 0 | 0 | 0 | 0 | 2C,9G | 5G | 1C,3G | 5C,9H | 2G | 2C,8G | 2C,9H | 1C,9G | |
| Sugar beets | | 2C,4G | | | 4C,9G | | | | | | | | |

| | Cmpd. 7 | | Cmpd. 8 | | Cmpd. 9 | Cmpd. 10 | Cmpd. 11 | Compound 12 | | Compound 13 | |
|---|---|---|---|---|---|---|---|---|---|---|---|
| Rate kg/ha | 0.05 | 0.4 | 0.05 | 0.4 | .05 | 0.05 | 0.05 | 0.05 | 5 | 0.05 | 5 |
| | | | | | POST-EMERGENCE | | | | | | |
| Bush bean | 9C | 9C | 9C | 9C | 9C | 6C,8G,6Y | 9C | 0 | 4C,7G,6Y | 2C | 2C,8G,6Y |
| Cotton | 9C | 9C | 10C | 10C | 6C,9G | 4C,9G | 5C,9G | 0 | 4C,7H | 2C | 3C,5G |
| Morningglory | 9C | 10C | 10C | 10C | 5C,9G | 9C | 9C | 4G | 5C,8H | 1C | 3C,7G |
| Cocklebur | 9C | 9C | 2C,7G | 9C | 5C,9G | 2C,9C | 2C,9G | 3G | 9C | 1C | 5C,9G |
| Sicklepod | | | | | 9C | 9C | 5C,9G | 0 | 2C,3G | 2C | 3C,5G |
| Cassia | 9C | 9C | 9C | 9C | | | | | | | |
| Nutsedge | 2C,6G | 3C,9G | 2C,9G | 7C,9G | 2C,7G | 1C,5G | 3C,9G | 0 | 3G | 0 | 5G |
| Crabgrass | 4C,9G | 9C | 2C,5G | 5C,8G | 1C,6G | 1C,6G | 2C,5G | 0 | 0 | 0 | 3C,7G |
| Barnyardgrass | 10C | 10C | 9C | 9C | 5C,9H | 2C,9H | 5C,9G | 0 | 0 | 0 | 5C,9H |
| Wild Oats | 5C,9G | 9C | 5C,9G | 9C | 3G | 0 | 2G | 0 | 0 | 0 | 2C,5G |
| Wheat | 9C | 9C | 10C | 9C | 0 | 1C,2G | 1C,4G | 0 | 0 | 0 | 1C,3G |
| Corn | 9C | 10C | 4C,9G | 9C | 5U,9G | 3C,9G | 2U,9G | 0 | 1H | 0 | 3C,9H |
| Soybean | 9C | 9C | 9C | 9C | 5C,9G | 9C | 6C,9G | 0 | 3C,8H | 1C,3H | 5C,9G |
| Rice | 6C,9G | 9C | 5C,9G | 5C,9G | 5C,9G | 5C,9G | 5C,8G | 0 | 2C,4G | 0 | 5C,9G |
| Sorghum | 9C | 10C | 5C,9G | 5C,9G | 2U,9G | 1C,6G | 2C,8G | 0 | 1C | 1C | 5C,7H |
| Sugar beets | | | | | 9C | 6C,9G | 5C,9G | 0 | 5C,9G | 1C | 5C,8H |

| | | Compound 14 | | Compound 15 | | Cmpd. 16 | Cmpd. 17 | Cmpd. 18 | Cmpd. 19 | Cmpd. 20 |
|---|---|---|---|---|---|---|---|---|---|---|
| | Rate kg/ha | 0.05 | 5 | 0.05 | 5 | 0.05 | 0.05 | 0.05 | 0.05 | 0.05 |
| | | | | | POST-EMERGENCE | | | | | |
| | Bush bean | 0 | 0 | 4C,9G,6Y | 3C,7G,6Y | 4C,9G,6Y | 0 | 0 | 3C,8G,6Y | 9C |
| | Cotton | 0 | 2C,3H | 0 | 2C | 3C,6G | 1C | 0 | 3C,5G | 5C,9G |
| | Morningglory | 1C | 5C,7H | 1C,3G | 2C | 5C,9G | 3C | 0 | 5C,9G | 5C,9G |
| | Cocklebur | 0 | 4C,9G | 3C,8H | 5C,9G | 3G | 0 | 3H | 1C | 4C,9G |
| | Sicklepod | 0 | 2C,3H | 0 | 3C | 1C | 2C | 0 | 2C | 3C,8G |
| | Nutsedge | 0 | 0 | 4G | 2C,5G | 2C,5G | 0 | 0 | 3C,5G | 4C,9G |
| | Crabgrass | 0 | 2G | 0 | 0 | 1C | 0 | 0 | 0 | 4G |
| | Barnyardgrass | 0 | 0 | 0 | 2C,2H | 2G | 1H | 0 | 0 | 5C,9H |
| | Wild Oats | 0 | 0 | 0 | 0 | 0 | 0 | 0 | 0 | 0 |
| | Wheat | 0 | 0 | 0 | 0 | 0 | 0 | 0 | 0 | 0 |
| | Corn | 0 | 0 | 0 | 0 | 0 | 0 | 0 | 0 | 3C,5G |
| | Soybean | 0 | 2C,4H | 8G | 3C,9G | 2C,8G | 1C,4G | 2H | 2C,8G | 5C,9G |
| | Rice | 0 | 2C,4G | 2G | 3C,6G | 6G | 1C,3G | 0 | 0 | 7G |
| | Sorghum | 0 | 2C | 0 | 2C | 2C,3G | 2G | 0 | 0 | 2C,9G |
| | Sugar beets | 0 | 3C,6G | 2G | 2C,5G | 5C,9G | 2G | 0 | 3C,9G | 3C,9G |

| | Cmpd. 1 | | Cmpd. 2 | | | Cmpd. 3 | | Cmpd. 4 | | Cmpd. 5 | | Cmpd. 6 | |
|---|---|---|---|---|---|---|---|---|---|---|---|---|---|
| Rate kg/ha | 0.4 | 10 | 0.05 | 0.4 | 10 | 0.05 | 0.4 | 0.4 | 0.05 | 0.4 | 0.05 | 0.4 | |
| | | | | | PRE-EMERGENCE | | | | | | | | |
| Morningglory | 0 | 3C,6H | 0 | 0 | 9G,3C | 7G | 8G | 9C | 1C | 3C,5G | 0 | 9C | |
| Cocklebur | 0 | 8H | 0 | — | 9H | 9H | 9H | 9H | 1C | 9H | 8H | 9H | |
| Cassia | 0 | 0 | 0 | 3G | 2C,9G | 9G | 9H | 3G | 1C | 8H | 5G | 7G | |
| Nutsedge | 0 | 0 | 0 | 0 | 5G | 10E | 10E | 1C,5G | 0 | 7G | 0 | 10E | |

TABLE A-continued

| | | | | | | | | | | | | |
|---|---|---|---|---|---|---|---|---|---|---|---|---|
| Crabgrass | 0 | 0 | 0 | 0 | 2C,4G | 1C | 2C | 2C,8G | 0 | 2G | 0 | 4G |
| Barnyardgrass | 0 | 2C | 0 | 0 | 2C,6G | 2C,5H | 2C,8H | 5C,8H | 0 | 5G | 2G | 8G |
| Wild Oats | 0 | 0 | 0 | 0 | 2C,5G | 0 | 1C,3G | 3C,8G | 0 | 2G | 0 | 3G |
| Wheat | 0 | 0 | 0 | 0 | 7G | 0 | 2G | 2C,9G | 0 | 2G | 0 | 1C,6G |
| Corn | 0 | 0 | 0 | 0 | 2C,8G | 1C,6G | 2C,9H | 3C,8H | 1C | 2C,5G | 3G | 8G |
| Soybean | 0 | 0 | 0 | 0 | 2C,6H | 2H | 7H | 2C,2H | 0 | 2C | 0 | 1C |
| Rice | 0 | 0 | 0 | 0 | 4C,8H | 2C,7H | 9H | 10E | 0 | 2C,8H | 5G | 10E |
| Sorghum | 0 | 0 | 0 | 0 | 4C,5H | 0 | 2C,5G | 5C,9G | 0 | 2C,6H | 3G | 2C,9G |
| Sugar beets | | 2C,5G | | 10E | 10E | | | | 1C | 10E | | |

| | Cmpd. 7 | | Cmpd. 8 | | Cmpd. 9 | Cmpd. 10 | Cmpd. 11 | Compound 12 | | Compound 13 | |
|---|---|---|---|---|---|---|---|---|---|---|---|
| Rate kg/ha | 0.05 | 0.4 | 0.05 | 0.4 | .05 | 0.05 | 0.05 | 0.05 | 5 | 0.05 | 5 |

PRE-EMERGENCE

| | | | | | | | | | | | |
|---|---|---|---|---|---|---|---|---|---|---|---|
| Morningglory | 9G | 5C,9G | 9G | 5C,9G | 9C | 10C | 9C | 1C,1H | 8H | 1C | 5C,9G |
| Cocklebur | 8H | 9H | 9H | — | 9H | — | — | 4G | 9H | 1H | 9H |
| Cassia | 9G | 2C,9G | 9G | 9G | | | | | | | |
| Sicklepod | | | | | 9C | 9C | 5C,9G | 1C,1H | 3C,8G | 0 | 5C,8H |
| Nutsedge | 7G | 10E | 9G | 10E | 2C,7G | 8G | 7G | 0 | 0 | 0 | 7G |
| Crabgrass | 2C,8G | 5C,9G | 5G | 5C,8G | 4C,5G | 4G | 5C,8G | 0 | 2G | 0 | 1C |
| Barnyardgrass | 3C,9H | 5C,9H | 5G | 4C,9H | 5C,9H | 5C,8G | 5C,9H | 0 | 0 | 0 | 3C,7H |
| Wild Oats | 3C,8H | 5C,8H | 5H | 3C,8G | 4C,5G | 2C,4G | 2C,7G | 0 | 0 | 0 | 3C,5G |
| Wheat | 3C,8G | 5C,9H | 1C,5G | 3C,9G | 1C,3G | 1C,5G | 1C,5G | 0 | 0 | 0 | 3C,5G |
| Corn | 5C,9G | 10H | 2C,7G | 3C,9G | 2C,9G | 2C,8G | 2C,8G | 0 | 2C,8G | 0 | 5C,9G |
| Soybean | 9H | 9H | 2C,4H | 9H | 9H | 9H | 9H | 0 | 3C,7G | 1C,1H | 3C,7H |
| Rice | 10E | 10E | 10E | 10E | 5C,9H | 5C,8G | 4C,8G | 0 | 3C,7G | 0 | 3C,9H |
| Sorghum | 5C,9H | 5C,9H | 1C,7G | 5C,9H | 2C,8G | 6G | 2C,7G | 3G | 2C,6H | 0 | 5C,9G |
| Sugar beets | | | | | 10E | 10E | 10E | 2H | 5C,9G | 0 | 5C,9G |

| | Compound 14 | | Compound 15 | | Cmpd. 16 | Cmpd. 17 | Cmpd. 18 | Cmpd. 19 | Cmpd. 20 |
|---|---|---|---|---|---|---|---|---|---|
| Rate kg/ha | 0.05 | 5 | 0.05 | 5 | 0.05 | 0.05 | 0.05 | 0.05 | 0.05 |

PRE-EMERGENCE

| | | | | | | | | | |
|---|---|---|---|---|---|---|---|---|---|
| Morningglory | 0 | 3C,7H | 2C,5H | 5C,9G | 8G | 3H | 2C | 9C | 9H |
| Cocklebur | 0 | 8H | 8H | 9H | 9H | 8H | 1C | 8H | 9H |
| Sicklepod | 0 | 3C | 2C | 8G | 8G | 1H | 1C | 8G | 8H |
| Nutsedge | 0 | 0 | 0 | 5G | 3G | 0 | 0 | 0 | 0 |
| Crabgrass | 0 | 0 | 2C | 2G | 2C | 0 | 2C | 0 | 0 |
| Barnyardgrass | 0 | 1C | 0 | 3C | 0 | 0 | 3C | 0 | 0 |
| Wild Oats | 0 | 1C,5G | 0 | 3C,8G | 0 | 0 | 1C | 0 | 0 |
| Wheat | 0 | 0 | 0 | 3G | 0 | 0 | 1C | 0 | 0 |
| Corn | 0 | 2C,4H | 0 | 2C,7G | 0 | 2C | 1C | 1C | 2C,5G |
| Soybean | 0 | 3C,4H | 1C | 2C,6H | 1H | 0 | 2C,5H | 1C | 3C,4H |
| Rice | 0 | 3C,7G | 0 | 3C,5G | 2G | 2G | 2C,3G | 2C | 3C,3G |
| Sorghum | 0 | 3C,6H | 0 | 3C | 0 | 1C | 2G | 0 | 1C,3G |
| Sugar beets | 0 | 8G | 2C,2H | 9G | 8G | 3G | 3G | 8G | 9H |

Test B

Two plastic bulb pans were filled with fertilized and limed Fallsington silt loam soil. Sometimes, Woodstown sandy loam is used as the growth medium. One pan was planted with corn, sorghum, Kentucky bluegrass and several grass weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dialatatum*), giant foxtail (*Setaria faberii*), cheatgrass (*Bromus secalinus*), mustard (*Brassica arvensis*), cocklebur (*Xanthium pensylvanicum*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated preemergence with several test compounds within the scope of the invention.

Twenty-eight days after treatment, the plants were evaluated and visually rated for response to the chemical treatments utilizing the rating system described previously for Test A. The data are summarized in Table B.

TABLE B

| | PRE-EMERGENCE ON FALLSINGTON SILT LOAM | | PRE-EMERGENCE ON WOODSTOWN SANDY LOAM | | | | | | | | |
|---|---|---|---|---|---|---|---|---|---|---|---|
| | Compound 4 | | Compound 9 | | Compound 10 | | Compound 11 | | Compound 19 | | Compound 20 | |
| Rate kg/ha | 0.06 | 0.25 | 0.03 | 0.125 | 0.03 | 0.125 | 0.03 | 0.125 | 0.03 | 0.125 | 0.03 | 0.125 |
| Crabgrass | 0 | 0 | 7G | 7G | 3G | 5G | 0 | 6G | 0 | 0 | 2G | 4G |
| Barnyardgrass | 0 | 0 | 8G | 9G | 6G | 7G | 4G | 6G | 0 | 0 | 2G | 7G |
| Sorghum | 0 | 3G | 9G | 10C | 6G | 8G | 6G | 6G | 0 | 0 | 3G | 9G |
| Wild Oats | 0 | 3G | 6G | 7G | 3G | 5G | 3G | 5G | 0 | 0 | 0 | 2G |
| Johnsongrass | 4G | 3G | 6G | 7G | 3G | 4G | 0 | 4G | 0 | 0 | 0 | 2G |
| Dallisgrass | 0 | 0 | 3G | 4G | 0 | 2G | 0 | 3G | 0 | 0 | 0 | 3G |
| Giant foxtail | 0 | 3G,3H | 5G | 8G | 6G | 7G | 0 | 8G | 0 | 0 | 4G | 6G |
| Ky. bluegrass | 0 | 3G | 7G | 9G | 4G | 7G | 0 | 6G | 0 | 0 | 0 | 0 |
| Cheatgrass | 0 | 0 | 8G | 9G | 2G | 7G | 0 | 7G | 0 | 0 | 3G | 8G |

TABLE B-continued

| | PRE-EMERGENCE ON FALLSINGTON SILT LOAM | | PRE-EMERGENCE ON WOODSTOWN SANDY LOAM | | | | | | | | | |
|---|---|---|---|---|---|---|---|---|---|---|---|---|
| | Compound 4 | | Compound 9 | | Compound 10 | | Compound 11 | | Compound 19 | | Compound 20 | |
| Rate kg/ha | 0.06 | 0.25 | 0.03 | 0.125 | 0.03 | 0.125 | 0.03 | 0.125 | 0.03 | 0.125 | 0.03 | 0.125 |
| Sugar beets | 5G | 7G,3H | 10C | 10C | 10C | 10C | 10C | 10C | 3G | 6G | 6G | 9G |
| Corn | 0 | 0 | 9G | 9G | 6G | 7G | 2G | 7G | 0 | 2G | 4G,2C | 6G,4C |
| Mustard | 5G,5C | 7G,8C | 10C | 10C | 9G,9C | 10C | 9G | 10C | 7G | 9G | 9G | 10C |
| Cocklebur | 3G,2C | 6G,3H | 7G | 8G | 7G | 7G | 6G | 7G | 0 | 0 | 8G | 9G |
| Nutsedge | — | — | 8G | 8G | 7G | 8G | 8G | 9G | 0 | 4G | 4G | 9G |
| Cotton | 5G | 5G,3H | 9G | 9G,9C | 7G | 9G | 7G | 9G | 0 | 2G | 2G | 8G |
| Morningglory | 3G | 4G,3H | 8G | 9G | 9G | 9G | 6G | 9G | 0 | 0 | 2G,2C | 8G |
| Sicklepod | 0 | 3G | 9G | 9G,9C | 9G | 9G | 7G | 8G | 0 | 2G | 4G | 7G |
| Teaweed | 0 | 0 | 8G | 9G | 8G | 9G | 6G | 9G | 0 | 2G | 0 | 5G |
| Velvetleaf | 4G,3H | 7G,5H | 7G | 9G | 9G | 9G,9C | 9G | 9G | 2G | 4G | 6G | 6G,3C |
| Jimsonweed | 0 | 3G | 9G | 9G,9C | 9G | 9G,9C | 9G | 9G | 0 | 3G | 5G | 7G |
| Soybean | 3G,2C | 4G,3C | 9G | 9G | 9G | 9G | 8G | 9G | 0 | 0 | 2C | 3G,3C |
| Rice | 0 | 6G,3H | 9G | 9G | 8G | 9G | 7G | 8G | 0 | 0 | 3G | 7G |
| Wheat | 0 | 2G | 5G | 5G | 4G | 5G | 4G | 4G | 0 | 0 | 0 | 0 |

Text C

The test chemicals, dissolved in a non-phytotoxic solvent, were applied in an overall spray to the foliage and surrounding soil of selected plant species. One day after treatment, plants were checked for rapid burn injury. Approximately fourteen days after treatment all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), cassia (*Cassia obtusifolia*), morningglory (*Ipomoea hederacea*), jimsonweed (*Datura stramonium*), cocklebur (*Xanthium pensylvanicum*), crabgrass (*Digitaria* sp.), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugar beets, and mustard. All plants were sprayed approximately 14 days after planting. Additional plant species are sometimes added to this standard test in order to evaluate unusual selectivity.

TABLE C

POST-EMERGENCE ON PLANTS GROWN IN WOODSTOWN SANDY LOAM SOIL

| | Compound 4 | |
|---|---|---|
| Rate, kg/ha | 0.03 | 0.12 |
| Soybeans | 8G,7C | 9G,7C |
| Velvetleaf | 9G | 10C |
| Sesbania | 8G,5C | 7G,5C |
| Sicklepod | 0 | 0 |
| Cotton | 7G | 7G |
| Morningglory | 9G,7C | 9G |
| Alfalfa | 7C | 7G |
| Jimsonweed | 0 | 1C |
| Cocklebur | 9G,5C | 9G,5C |
| Corn | 1U | 1G,1C |
| Crabgrass | 3G,2C | 0 |
| Rice | 8G,7C | 9G,7C |
| Nutsedge | 2G | 7G |
| Barnyardgrass | 0 | 7G |
| Wheat | 0 | 0 |
| Giant Foxtail | 7G | 1C |
| Wild Oats | 0 | 8G,1C |
| Sorghum | 1C | 5G,4C |
| Sunflower | 10C | 10C |
| Mustard | — | 9G,9C |
| Sugar beets | 10C | 7G |

Test D

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), smartweed (*Polygonum pensylvanicum*), tumble mustard (*Sisymbrium altissimum*) kochia (*Kochia scoparia*), shepherd's purse (*Capsella bursa-pastoris*), Matricaria inodora, black nightshade (*Solanum nigrum*), yellow rocket (*Barbarea vulgaris*), wild mustard (*Brassica kaber*) and wild buckwheat (*Polygonum convolvulus*). The above two pans were treated pre-emergence. At the same time two pans in which the above plant species were growing were treated post-emergence. Plant height at the time of treatment ranged from 1–15 cm depending on plant species.

The compounds applied were diluted with a non-phytotoxic solvent and sprayed over-the-top of the pans. An untreated control and a solvent-alone control were included for comparison. All treatments were maintained in the greenhouse for 19–21 days at which time the treatments were compared to the controls and the effects visually rated. The recorded data are presented in Table D.

TABLE D

| | Compound 4 | | | |
| --- | --- | --- | --- | --- |
| | Pre-Emergence | | Post-Emergence | |
| Rate kg/ha | 0.015 | 0.06 | 0.015 | 0.06 |
| wheat | 0 | 1G | 1G | 2C,2G |
| barley | 0 | 2G | 3G | 4G |
| wild oats | 0 | 0 | 3G | 1C,5G |
| downy brome | 3G | 7G | 0 | 8G |
| cheatgrass | 1G | 6G | 0 | 6G |
| blackgrass | 0 | 7G | 0 | 4G |
| annual bluegrass | 0 | 1C,6G | 2C,2G | 2C,5G |
| green foxtail | 0 | 7C,3G | 4G | 6G |
| quackgrass | 0 | 4G | 1C,2G | 1C,4G |
| Italian ryegrass | 0 | 6G | 2G | 7C,8G |
| ripgut brome | 0 | 5G | 2G | 2C,7G |
| Russian thistle | 0 | 1C,2G | 0 | 2C,2G |
| tansy mustard | 0 | 10C | 5C,3G | 10C |
| smartweed | — | — | — | 9C,9G |
| tumble mustard | 0 | 10C | 3C,6G | 10C |
| kochia | 0 | 5G | 0 | 4C,7G |
| shepherd's purse | 3C,6G | 10C | 1C,2G | 10C |
| *Matricaria inodora* | — | — | 10C | 10C |
| black nightshade | 1C,1G | 5C,8G | 6G | 4C,7G |
| yellow rocket | 2G | 3C,7G | 0 | 9C,9G |
| wild mustard | 1C,4G | 10C | 2C,5G | 10C |
| wild buckwheat | 0 | 1C,2G | 0 | 2G |

What is claimed is:

1. A compound of the formula:

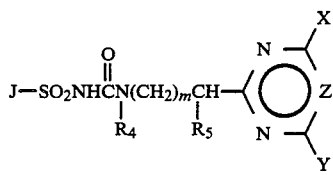

wherein
J is

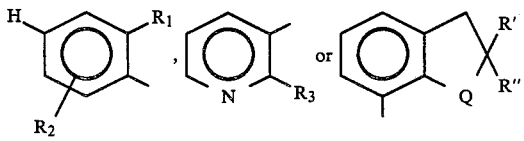

$R_1$ is $NO_2$, F, Cl, Br, $CF_3$, $C_1$-$C_3$ alkyl, $CH_2CH_2OCH_3$, $CO_2R_6$, $S(O)_nR_7$, $SO_2NR_8R_9$, $SCF_2H$, $OR_{10}$, $OSO_2R_{11}$,

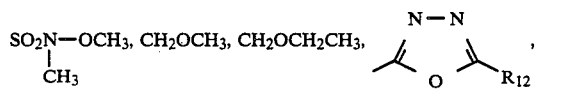

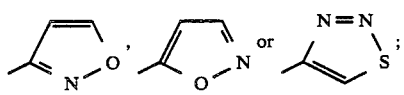

$R_2$ is H;
$R_3$ is Cl, $SO_2CH_3$ or $SO_2N(CH_3)_2$;
$R_4$ and $R_5$ are independently H or $CH_3$;
$R_6$ is $C_1$-$C_3$ alkyl, $CH_2CH=CH_2$, $CH_2CH_2Cl$ or $CH_2CH_2OCH_3$;
$R_7$ is $C_1$-$C_3$ alkyl or $CH_2CH=CH_2$;
$R_8$ is $CH_3$;
$R_9$ is $C_1$-$C_3$ alkyl;
$R_{10}$ is $C_1$-$C_3$ alkyl, $CF_2H$ or $CH_2CH_2OCH_3$;
$R_{11}$ is $C_1$-$C_3$ alkyl;
$R_{12}$ is H or $CH_3$;
n is 0 or 2;
m is 0;
Q is O, S or $SO_2$;
R' is H or $CH_3$;
R" is H or $C_1$-$C_3$ alkyl;
Z is CH;
X is $CH_3$ or $OCH_3$;
Y is $CH_3$, $C_2H_5$, $OCH_3$, $OC_2H_5$, $CH_2OCH_3$, $CH(OCH_3)_2$ or

provided that
(1) $R_4$ and $R_5$ cannot simultaneously be $CH_3$; and
(2) when X and Y are both $CH_3$ then $R_1$ must be other than $NO_2$, $S(O)_nR_7$ or $C_1$-$C_3$ alkyl;
and their agriculturally suitable salts.

2. A compound of claim 1 where $R_4$ and $R_5$ are H, and X is $OCH_3$.

3. A compound of claim 2 where Y is $CH_3$, $C_2H_5$, $CH_3O$ or $C_2H_5O$.

4. A compound of claim 3 where J is

5. A compound of claim 4 where $R_1$ is $CO_2CH_3$, $CO_2C_2H_5$, $SCF_2H$, $OSO_2CH_3$ or $SO_2N(CH_3)_2$.

6. The compound of claim 1 which is methyl 2-[N-[(4,6-dimethoxyprimidin-2-yl)methylaminocarbonyl]aminosulfonyl]benzoate.

7. The compound of claim 1 which is N'-[(4,6-dimethylpyrimidin-2-yl)methylaminocarbonyl]-N,N-dimethyl-1,2-benzenedisulfonamide.

8. The compound of claim 1 which is N'-[(4,6-dimethoxyprimidin-2-yl)methylaminocarbonyl]-N,N-dimethyl-1,2-benzenedisulfonamide.

9. The compound of claim 1 which is N'-[(4-methoxy-6-methylpyrimidin-2-yl)methylaminocarbonyl]-N,N-dimethyl-1,2-benzenedisulfonamide.

10. A composition suitable for controlling the growth of undesired vegetation which comprises an effective amount of a compound of claim 1 and at least one of the following: surfactant, solid or liquid inert diluent.

11. A composition suitable for controlling the growth of undesired vegetation which comprises an effective amount of a compound of claim 2 and at least one of the following: surfactant, solid or liquid inert diluent.

12. A composition suitable for controlling the growth of undesired vegetation which comprises an effective amount of a compound of claim 3 and at least one of the following: surfactant, solid or liquid inert diluent.

13. A composition suitable for controlling the growth of undesired vegetation which comprises an effective amount of a compound of claim 4 and at least one of the following: surfactant, solid or liquid inert diluent.

14. A composition suitable for controlling the growth of undesired vegetation which comprises an effective amount of a compound of claim 5 and at least one of the following: surfactant, solid or liquid inert diluent.

15. A method for controlling the growth of undesired vegetation which comprises applying to the locus to be protected an effective amount of a compound of claim 1.

16. A method for controlling the growth of undesired vegetation which comprises applying to the locus to be protected an effective amount of a compound of claim 2.

17. A method for controlling the growth of undesired vegetation which comprises applying to the locus to be protected an effective amount of a compound of claim 3.

18. A method for controlling the growth of undesired vegetation which comprises applying to the locus to be protected an effective amount of a compound of claim 4.

19. A method for controlling the growth of undesired vegetation which comprises applying to the locus to be protected an effective amount of a compound of claim 5.

* * * * *